US009479851B2

(12) United States Patent
Osawa et al.

(10) Patent No.: US 9,479,851 B2
(45) **Date of Patent: *Oct. 25, 2016**

(54) VEHICLE SOUND GENERATION APPARATUS, AND VEHICLE SOUND GENERATION METHOD

(71) Applicants: Yamaha Hatsudoki Kabushiki Kaisha, Iwata-shi, Shizuoka (JP); Yamaha Corporation, Hamamatsu-shi, Shizuoka (JP)

(72) Inventors: Hideki Osawa, Shizuoka (JP); Heiji Maruyama, Shizuoka (JP); Yasuyuki Suzuki, Shizuoka (JP); Yosuke Kuno, Shizuoka (JP); Hirofumi Onitsuka, Shizuoka (JP); Yoshikazu Honji, Shizuoka (JP)

(73) Assignees: YAMAHA HATSUDOKI KABUSHIKI KAISHA, Shizuoka (JP); YAMAHA CORPORATION, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/394,537

(22) PCT Filed: Apr. 16, 2013

(86) PCT No.: PCT/JP2013/061271

§ 371 (c)(1),
(2) Date: Oct. 15, 2014

(87) PCT Pub. No.: WO2013/157539

PCT Pub. Date: Oct. 24, 2013

(65) Prior Publication Data

US 2015/0092957 A1 Apr. 2, 2015

(30) Foreign Application Priority Data

Apr. 16, 2012 (JP) ................................ 2012-093109

(51) Int. Cl.
*H04B 1/00* (2006.01)
*A61F 11/06* (2006.01)
(Continued)

(52) U.S. Cl.
CPC ............ *H04R 1/00* (2013.01); *F02M 35/1038* (2013.01); *F02M 35/1294* (2013.01); *G10K 15/02* (2013.01); *G10K 2210/12822* (2013.01)

(58) Field of Classification Search
CPC ..... B60Q 5/00; B60R 11/0217; F01N 1/065; F02M 35/1038; F02M 35/1294; F02M 35/021; G10K 15/02; G10K 2210/112; G10K 2210/12822; H04R 1/00; H04R 2499/13
USPC ....................................... 381/86, 94, 7, 71.4
See application file for complete search history.

(56) References Cited

U.S. PATENT DOCUMENTS

| | | | | |
|---|---|---|---|---|
| 4,428,227 A * | 1/1984 | Yamagata | G01L 23/24 | 73/114.37 |
| 5,850,458 A * | 12/1998 | Tomisawa | G10K 11/1786 | 381/71.4 |

(Continued)

FOREIGN PATENT DOCUMENTS

| | | |
|---|---|---|
| JP | 02-041953 A | 2/1990 |
| JP | 2002-520680 A | 7/2002 |

(Continued)

OTHER PUBLICATIONS

Osawa et al.; "Sound Generating Device for Vehicle, and Sound Generating Method for Vehicle"; U.S. Appl. No. 13/883,614, filed May 6, 2013.

(Continued)

*Primary Examiner* — Vivian Chin
*Assistant Examiner* — Douglas Suthers
(74) *Attorney, Agent, or Firm* — Keating and Bennett, LLP

(57) ABSTRACT

A vehicle sound generation apparatus 20 is constituted by a first pressure sensor 21*a*, a second pressure sensor 21*b*, a signal processing section 24 which performs processing of changing pressure signals output from the first pressure sensor 21*a* and the second pressure sensor 21*b* in accordance with the operation state of an automobile 10, and speakers 28*a*, 28*b* which output, as an intake sound of an engine 12, a sound pressure signal processed by the signal processing section 24. The first pressure sensor 21*a* is provided on an intake duct 15 connecting an air cleaner 16 and a throttle body 17 at a position between the air cleaner 16 and the center of the intake duct 15, and the second pressure sensor 21*b* is provided between the engine 12 and the throttle body 17.

17 Claims, 14 Drawing Sheets

(51) Int. Cl.

| | |
|---|---|
| ***G10K 11/16*** | (2006.01) |
| ***H03B 29/00*** | (2006.01) |
| ***H04B 15/00*** | (2006.01) |
| ***H04R 1/00*** | (2006.01) |
| ***G10K 15/02*** | (2006.01) |
| ***F02M 35/10*** | (2006.01) |
| ***F02M 35/12*** | (2006.01) |

(56) References Cited

U.S. PATENT DOCUMENTS 5,967,129 A * 10/1999 Yamashita .......... F02D 41/1495
123/674
7,088,829 B1 * 8/2006 Schick ..................... B60Q 5/00
381/61
2005/0094826 A1 5/2005 Morishita
2010/0286944 A1 * 11/2010 Reihlen .................. G01D 15/00
702/122
2013/0230185 A1 9/2013 Osawa et al.

FOREIGN PATENT DOCUMENTS

| | | | |
|---|---|---|---|
| JP | 2005-134749 | A | 5/2005 |
| JP | 2005-282526 | A | 10/2005 |
| JP | 2007-212616 | A | 8/2007 |
| JP | 2008-013064 | A | 1/2008 |
| WO | 2012/141325 | A1 | 10/2012 |
| WO | 2012/141326 | A1 | 10/2012 |

OTHER PUBLICATIONS

Official Communication issued in International Patent Application No. PCT/JP2013/061271, mailed on Jul. 23, 2013.

* cited by examiner (a)

(b)

VEHICLE SOUND GENERATION APPARATUS, AND VEHICLE SOUND GENERATION METHOD

TECHNICAL FIELD

The present invention relates to a vehicle sound generation apparatus and a vehicle sound generation method for transmitting the intake sound of an engine of a vehicle to an occupant inside the vehicle.

BACKGROUND ART

A recent vehicle such as an automobile is designed so as to minimize engine sound and sounds generated as a result of travel of the vehicle, to thereby make occupants more comfortable and to prevent radiation of noise to the outside of the vehicle. However, such design brings about a problem in that the relation between the actual traveling conditions (vehicle speed, etc.) and the sound heard by the occupants becomes weak, and drive feeling deteriorates. In order to solve such a problem, there has been developed a vehicle sound generation apparatus which causes a speaker to produce an engine sound toward the interior of the vehicle cabin without radiating any sound to the outside of the vehicle. Such an apparatus is disclosed in, for example, Japanese Patent Application Laid-Open (kokai) No. 2008-13064.

This vehicle sound generation apparatus (operating sound transmission apparatus) includes a sound pressure sensor disposed at an intake air introduction port or inside an intake pipe of an engine; a rotary pulse sensor for detecting ignition pulses of the engine; an accelerator opening sensor for detecting an amount by which an accelerator pedal is pressed down; a speaker and a controller which are disposed in the engine compartment or the cabin and produces an operating sound of the engine. The controller includes an order filter which changes a sound wave signal output from the sound pressure sensor and passing therethrough, in accordance with an input frequency from the rotary pulse sensor; and a level adjustor which increases and decreases the level of the sound wave signal having passed through the order filter in accordance with an opening signal from the accelerator opening sensor. The sound wave signal output from the controller is amplified by an amplifier and is output from the speaker.

However, in the case of the above-described conventional vehicle sound generation apparatus, a plurality of sound pressure sensors are attached to an external air introduction port of an air cleaner and an external air introduction port of an air duct disposed on the upstream side of the air cleaner. Or, a plurality of sound pressure sensors are attached to an intake manifold. Therefore, in the case where sound pressure sensors are attached to the air cleaner and the external air introduction port of the air cleaner, the detection of the sound pressure of intake sound is difficult, because the intake sound is of low level. As a result, an apparatus for accurately reproducing intake sound is required. In the case where sound pressure sensors are attached to the intake manifold, since the sound pressure sensors are located near the engine, which generates explosion sound, the variation of pulsation becomes large, which raises a problem in that the sound produced by the speaker becomes rough and irritating.

Moreover, in the case where microphones are used as sound pressure sensors and are attached to the air cleaner and the external air introduction port of the air cleaner, the microphones detect external sounds in addition to intake sound, which raises a problem of difficulty in obtaining a desired engine intake sound. Also, there arises a problem in that it is difficult for microphones to maintain their performances over a long period of time in a severe environment in the engine compartment in which parts must have durability against heat, water, oil, and dust.

SUMMARY OF THE INVENTION

The present invention has been accomplished in order to solve the above-described problems, and its object is to provide a vehicle sound generation apparatus and a vehicle sound generation method which detect the pressure of intake pulsation on the upstream and downstream sides of an intake duct, to thereby enable generation of comfortable sound inside a vehicle, the sound closely resembling the actual intake sound of an engine and being low in noise level. Notably, in the following description of constituent elements of the present invention, in order to facilitate understanding of the present invention, symbols representing corresponding portions of an embodiment are described in parentheses. However, the constituent elements of the present invention should not be construed to be limited to the configurations of the corresponding portions of the embodiment denoted by the symbols.

In order to achieve the above-described object, the present invention provides a vehicle sound generation apparatus (20, 40, 50, 60) for transmitting intake sound of an engine (12, 72, 83, 102) of a vehicle (10, 100) to an occupant in the vehicle, comprising:

a first pressure sensor (21*a*, 61*a*, 81*a*) which is provided on an intake duct (15, 85) which connects together an air cleaner (16, 86) provided on a side toward an intake port for introducing external air and a throttle body (17, 77*a*, 87) provided on a side toward the engine, the first pressure sensor being located on the air cleaner side of a midpoint between the air cleaner and a throttle valve (77*b*) provided in the throttle body, detecting pressure of intake pulsation of the engine, and outputting a pressure signal representing the detected pressure;

a second pressure sensor (21*b*, 61*b*, 71*b*, 81*b*) which is provided between the engine and the throttle valve and which detects the pressure of the intake pulsation of the engine and outputs a pressure signal representing the detected pressure;

a signal processing section (24) which performs processing of changing the pressure signals output from the first and second pressure sensors in accordance with an operation state of the vehicle; and a speaker (28*a*, 28*b*, 108*a*, 108*b*) disposed in the vehicle and outputting the pressure signals processed by the signal processing section as an intake sound of the engine.

The vehicle sound generation apparatus of the present invention allows a driver to clearly hear the intake sound of the engine corresponding to the operation state which changes as a result of operation by a driver, while radiating the intake sound to the outside at a low level. Also, in the present invention, the first pressure sensor is provided on the intake duct connecting the throttle valve and the air cleaner together such that the first pressure sensor is located at an air-cleaner-side portion of the intake duct. Therefore, it becomes possible to effectively detect the pressure variation of the intake pulsation without being influenced by the sound coming from outside the vehicle (e.g., wind noise) and the drive sound and explosion sound of the engine. Thus, the sound that the occupant hears inside the vehicle becomes close to the actual intake sound of the engine.

Also, since the second pressure sensor is provided between the engine and the throttle valve so as to detect the intake pulsation at that section, the intake sound reproduced by the speaker corresponds to the intake pulsation of the engine irrespective of whether the throttle valve is opened or closed. For example, in the case where only the first pressure sensor is provided on the upstream side of the throttle valve, the following problem occurs. In a state in which the throttle valve is closed almost completely or is opened only slightly at the time of, for example, idling, deceleration, or light load, transmission of intake pulsation of the engine, which is produced as a result of opening and closing of intake valves, to the upstream side is restricted by the throttle valve. Therefore, the pressure change of the intake pulsation of the engine is very small in the intake duct located upstream of the throttle valve, and the first pressure sensor encounters a difficulty in detecting the intake pulsation.

However, on the downstream side of the throttle valve, the pressure change of the intake pulsation of the engine is larger than that on the upstream side of the throttle valve. Therefore, sound of intake pulsation of the engine can be generated on the basis of the pressure detected by the second pressure sensor. Thus, it becomes possible to enhance the sound reproduced by the speaker at the time of idling or the like, to thereby allow the driver to always hear the sound corresponding to the operation of the engine inside the vehicle.

Notably, the engine sound actually heard during a travel of the vehicle is dominated by a component which is heard from the external side; i.e., the upstream side of the air cleaner. Therefore, according to the present invention, the intake sound reproduced by the speaker becomes close to the actual intake sound. Moreover, in the present invention, the first pressure sensor and the second pressure sensor are provided on the upstream and downstream sides, respectively, of the throttle valve. Therefore, even at the time of light load when the depressing amount of the accelerator pedal is small, intake pulsation can be detected effectively.

Another configurational feature of the vehicle sound generation apparatus according to the present invention is further comprising a noise gate processing section (42) which performs noise gate processing on the pressure signals before being processed by the signal processing section. In this case, the pressure signals having undergone the noise gate processing may be subjected to A/D conversion before being processed by the signal processing section. The vehicle sound generation apparatus according to the present invention can generate a natural sound while removing noise in an unnecessary region. Notably, the noise gate processing may be performed on the pressure signals having undergone A/D conversion.

Another configurational feature of the vehicle sound generation apparatus according to the present invention is further comprising a noise suppression processing section (43) which performs noise suppression processing on the pressure signals before or after being processed by the signal processing section. In this case, preferably, the noise suppression processing is performed on the pressure signals before being processed by the signal processing section. The noise suppression processing according to the present invention is performed through, for example, spectral subtraction, which makes it possible to generate a natural sound while removing noise in an unnecessary region.

Another configurational feature of the vehicle sound generation apparatus according to the present invention is further comprising a filer (25) prepared on the basis of a relation between frequency and gain, wherein the signal processing section performs the processing of changing the pressure signals by using the filer. According to the present invention, the gain can be changed freely in accordance with the frequency. Preferably, a plurality of types of filters are prepared, and the tone of the intake sound generated by the speaker can be changed among various types of tones (e.g., engine sound of a normal car and engine sound of a sports car) by selecting one of the filters.

Another configurational feature of the vehicle sound generation apparatus according to the present invention is further comprising a rotation sensor (31, 103) for detecting rotational speed of the engine, an opening sensor (32) for detecting opening of the throttle valve, and a sound pressure amplification map (25*a*) prepared on the basis of a relation between the rotational speed of the engine detected by the rotation sensor and the throttle opening detected by the opening sensor, wherein the signal processing section performs sound pressure amplification processing on the pressure signals by using the sound pressure amplification map.

According to the present invention, on the basis of the value of the rotational speed of the engine detected by the rotation sensor and the value of the throttle opening detected by the opening sensor, the sound pressure amplification processing can be performed on the pressure signals output from the first pressure sensor and the second pressure sensor, or the gain of filter processing for processing the pressure signals output from the first pressure sensor and the second pressure sensor can be increased throughout the entire frequency range. Although the sound pressure amplification map can be prepared freely, preferably, the sound pressure amplification map is prepared to provide a large degree of amplification when the rotational speed of the engine is low and the load of the engine is small and provide a small degree of amplification when the rotational speed of the engine is high and the load of the engine is large. Also, according to the present invention, the speaker can reproduce in the cabin an intake sound whose attenuation characteristic and transmission loss are similar to those of the actual intake sound of the engine. Notably, the opening sensor may be a sensor which directly detects the rotational angle of the throttle valve or a sensor which detects the depressing amount of the accelerator pedal as the throttle opening.

Another configurational feature of the vehicle sound generation apparatus according to the present invention is further comprising a rotation sensor for detecting the rotational speed of the engine and a gain adjustment map (25*b*) which is prepared on the basis of a relation between frequency and gain, wherein the signal processing section obtains a frequency from the rotational speed of the engine detected by the rotation sensor and the number of cylinders of the engine, and adjusts a gain for the pressure signals by using the obtained frequency and the gain adjustment map. In this case, preferably, the frequency is a ⅓ octave center frequency. However, the width of the frequency band where gain adjustment is performed may be greater or less than ⅓ octave. Even in such a case, an advantageous effect is achieved, although the degree of the effect may change depending on the width.

According to the present invention, the N-th order (N: integer) frequency component of the fundamental explosion frequency of the engine which changes in accordance with the number of the cylinders of the engine can be enhanced. The frequency can be calculated from the rotational speed of the engine and the number of cylinders of the engine, and the pressure signals can be enhanced in accordance with the N-th order frequency component determined from the rotational speed of the engine, by increasing the gain in a frequency region corresponding to the rotational speed of the engine by using the gain adjustment map. For example, in the case of a four-cycle engine, since explosion occurs within a cylinder one time per two rotations of the crankshaft of the engine, the basic frequency becomes half of a frequency corresponding to the rotation speed of the engine.

In the case where the engine has four cylinders and explosion occurs in these cylinders at equal intervals without overlapping, the frequency becomes four times the frequency corresponding to the rotation speed of the engine. The frequency used for gain adjustment can be obtained from the frequency calculated in the above-described manner. Notably, it is difficult for the ears of the human being to distinguish sounds which differ slightly in frequency. However, if the sounds have a frequency difference of about ⅓ of one octave, the ears of the human being can quite clearly distinguish the sounds from each other. Therefore, when the gain adjustment map is prepared on the basis of the relation between the gain and the ⅓ octave center frequency, it becomes possible to perform the processing of the pressure signals at a level matching the sense of hearing of the human being, which is more effective.

Another configurational feature of the vehicle sound generation apparatus according to the present invention is further comprising a rotation sensor for detecting the rotational speed of the engine, an opening sensor for detecting the opening of the throttle valve, and an effector processing map (25*c*) which is prepared on the basis of a relation between the rotational speed of the engine detected by the rotation sensor and the throttle opening detected by the opening sensor and which has a compressor processing region and a reverberator processing region, wherein the signal processing section performs compressor processing or reverberator processing on the pressure signals by using the effector processing map.

In this case, preferably, the compressor processing is performed when both of the value of the rotational speed of the engine detected by the rotation sensor and the value of the throttle opening detected by the opening sensor are small, and reverberator processing is performed when one or both of the value of the rotational speed of the engine detected by the rotation sensor and the value of the throttle opening detected by the opening sensor are large.

According to the present invention, the compressor processing or the reverberator processing is performed on the pressure signals output from the first pressure sensor and the second pressure sensor, or on the pressure signals which is obtained by processing the pressure signals output from the first pressure sensor and the second pressure sensor on the basis of the filter characteristic, in accordance with the operation state of the vehicle. Thus, it is possible to enhance the sound pressure and to exert a reverberation effect on the intake sound produced by the speakers such that the occupant feels the intake sound being prolonged and continuing. In this case, the compressor processing for enhancing the sound pressure is performed at the time of low rotational speed and low load (when both of the value of the rotational speed of the engine detected by the rotation sensor and the value of the throttle opening detected by the opening sensor are small).

Also, the reverberator processing is performed at the time of high rotational speed (when the value of the rotational speed of the engine detected by the rotation sensor is large), at the time of high load (when the value of the throttle opening detected by the opening sensor is large), and at the time of high rotational speed and high load (when both of the values are large). Thus, the intake sound generated by the speaker can be made comfortable. Notably, when the compressor processing is performed at the time of high rotational speed or at the time of high load, a portion whose sound pressure level is high is compressed, and the generated intake sound becomes unable to cause the occupant to feel the intake sound being prolonged and continuing. Therefore, in this state, the reverberator processing is performed to cause the occupant to feel the intake sound being prolonged and continuing.

Another configurational feature of the vehicle sound generation apparatus according to the present invention is further comprising an acceleration sensor (51) for detecting acceleration of the vehicle and a sound pressure amplification map (25*a*) which is prepared on the basis of the acceleration of the vehicle detected by the acceleration sensor, wherein the signal processing section performs sound pressure amplification processing on the pressure signals by using the sound pressure amplification map.

According to the present invention, on the basis of the value of the acceleration of the vehicle detected by the acceleration sensor, the sound pressure amplification processing can be performed on the pressure signals output from the pressure sensors, or the gain of filter processing for processing the pressure signals output from the pressure sensors can be increased throughout the entire frequency range. In this case, since the acceleration sensor can be attached to an arbitrary location of the vehicle, the vehicle is not required to be modified, and wiring does not become complicated. Therefore, installation of the acceleration sensor becomes easier.

Another configurational feature of the vehicle sound generation apparatus according to the present invention resides in that an air flow meter (18, 89) for detecting the flow rate of air is provided on the intake duct to be located in the vicinity of and on the downstream side of the air cleaner, and the first pressure sensor is provided at a position which is offset from the air flow meter toward the throttle valve by an amount of 20 cm or less. According to the present invention, it is possible to detect the pulsation of intake pressure produced in the intake duct by using the first pressure sensor, while reducing noise. Variety of intake ducts having different lengths exist. The results of an experiment show that, even in the case where a short intake duct was used, a good result was attained when the first pressure sensor was provided at a position offset from the air flow meter toward the throttle valve by an amount of 20 cm or less.

Another configurational feature of the vehicle sound generation apparatus according to the present invention is further comprising a communication portion (29*a*) which extends outward from a circumferential wall of the intake duct, wherein a pressure sensing portion (21*c*) of the first pressure sensor is disposed at a distal end of the communication portion, and a passage length of the communication portion between its base end portion (15*a*) on the intake duct side and the pressure sensing portion (21*c*) of the first pressure sensor is set to a length equal to or less than a length which causes resonance.

When the frequency of change of the pressure detected by the first pressure sensor is equal to or higher than, for example, 2 kHZ, a sound which is uncomfortable for the occupant may be reproduced. Also, in general, each pressure sensor outputs a pulsating signal including a DC component when it detects a change in pressure. However, if this signal is used as an acoustic signal as is, a problem arises, because the acoustic signal is usually composed of an AC component only. Therefore, in the present invention, in order to prevent generation of uncomfortable sound and to obtain a signal which can be handled by ordinary acoustic equipment, there are employed a high pass filter which cuts components whose frequencies are equal to or lower than a very low frequency (e.g., 1 HZ), and a low pass filter which cuts components whose frequencies are equal to higher than 2 kHZ. Also, a pressure sensor whose sensitivity range is 1 HZ to 2 kHZ may be used as the first pressure sensor.

In these cases, by setting the length of the communication portion between the base end portion on the intake duct side and the pressure sensing portion of the first pressure sensor to, for example, 4 cm or less, it is possible to prevent occurrence of resonance at the communication portion between the base end portion on the intake duct side and the pressure sensing portion of the first pressure sensor. Namely, when the sound velocity of the intake sound is 340 m/s and the required upper limit frequency of the intake sound is 2 kHZ, the wavelength is 170 mm (the sound velocity/the frequency). In the case of a tubular body whose one end is open and whose other end is closed, such as the communication portion connecting the intake duct and the first pressure sensor, resonance occurs when the length of the tubular body is equal to or greater than ¼ of the wavelength; i.e., when the length is 42.5 mm or greater.

Therefore, the distance between the base end portion on the intake duct side and the pressure sensing portion of the first pressure sensor is set to 4 cm or less in consideration of some margin. Thus, the communication portion can be made shorter than ¼ of the wavelength corresponding to the required upper limit frequency. Thus, occurrence of resonance can be prevented. According to the present invention, an adverse effect on the detection by the first pressure sensor can be prevented by providing the first pressure sensor via the communication portion.

Another configurational feature of the vehicle sound generation apparatus according to the present invention is further comprising a communication portion (29*b*) which extends outward from a portion (14, 74*d*, 84) which is located between the engine and the throttle valve and to which the second pressure sensor is attached, wherein a pressure sensing portion of the second pressure sensor is disposed at a distal end of the communication portion, and a passage length of the communication portion between its base end portion and the pressure sensing portion of the second pressure sensor is set to a length equal to or greater than the passage length of the communication portion for the first pressure sensor between the base end portion and the pressure sensing portion of the first pressure sensor. According to the vehicle sound generation apparatus of the present invention, the length of the tubular communication portion for attaching the second pressure sensor is made longish, whereby sound produced as a result of rough pulsation of the engine can be attenuated for mitigation.

Another configurational feature of the vehicle sound generation apparatus according to the present invention resides in that each of the first pressure sensor and the second pressure sensor measures both of positive and negative pressures. In the case where sensors which can measure negative pressure only are used as the first pressure sensor and the second pressure sensor, when a positive pressure is generated (for example, when the accelerator pedal is pressed down suddenly), the speaker may generate a distorted sound or a crackling sound. In the vehicle sound generation apparatus according to the present invention, each of the first pressure sensor and the second pressure sensor measures both of positive and negative pressures. Therefore, even in the full-load transition period, the intake pulsation can be detected accurately without eliminating it, whereby generation of a distorted sound or a crackling sound can be prevented.

Another configurational feature of the vehicle sound generation apparatus according to the present invention resides in that the DC component of a signal output from the first pressure sensor (61*a*) is removed by a filer, and the second pressure sensor (61*b*) outputs a pulsating signal including an AC component and a DC component.

Since an acoustic signal is usually composed of an AC component only, it is not preferred to use a signal containing a DC component as an acoustic signal as is. According to the vehicle sound generation apparatus of the present invention, since the DC component of the signal output from the first pressure sensor is removed by a filer, generation of uncomfortable sound is prevented, whereby a desired acoustic signal can be obtained. Meanwhile, the second pressure sensor outputs a pulsating signal including an AC component and a DC component. In this case, preferably, noise suppression processing is performed on the AC component of the output signal. Thus, the rotational speed of the engine can be determined from the AC component of the signal output from the second pressure sensor, and the load of the engine can be determined from the DC component of the signal output from the second pressure sensor. Accordingly, it is possible to increase and decrease the sound pressure properly while judging the operation state from these pieces of information.

Another configurational feature of the vehicle sound generation apparatus according to the present invention resides in that the engine (72) is an independent throttle type in which throttle bodies (77*a*) are independently provided for cylinders, the throttle bodies communicate with one another through a balance pipe portion (77*d*) on the downstream side of the throttle valves (77*b*) provided in the throttle bodies (77*a*), and the second pressure sensor (71*d*) is provided on the balance pipe portion.

The vehicle sound generation apparatus of the present invention allows a driver to clearly hear the intake sound of the engine corresponding to the operation state which changes as a result of operation by the driver, while radiating the intake sound to the outside at a low level, even in the case where the engine is an independent throttle type. Also, since the second pressure sensor is provided on the balance pipe portion, the intake pulsations of all the cylinders of the engine can be detected (in the case of a V-type engine, all the cylinders of one bank). Notably, in the present invention, the intake duct refers to a portion between the throttle body and the air cleaner. In the case where a surge tank is located between the throttle body and the air cleaner, the surge tank is considered to be a part of the intake duct.

Another configurational feature of the vehicle sound generation apparatus according to the present invention resides in that the engine (83) has a turbo charger including a compressor (82*a*) located at an intermediate portion of the intake duct (85), and the first pressure sensor (81*a*) is provided at a position between the compressor and the air cleaner. The vehicle sound generation apparatus of the present invention allows a driver to clearly hear the intake sound of the engine corresponding to the operation state which changes as a result of operation by the driver, while radiating the intake sound to the outside at a low level, even in the case where the vehicle has a turbo charger.

The present invention provides a vehicle sound generation method for transmitting intake sound of an engine of a vehicle to an occupant in the vehicle, comprising:

a pressure signal output step of detecting pressure of intake pulsation of the engine by using first and second pressure sensors and outputting pressure signals representing the detected pressures, the first pressure sensor being provided on an intake duct which connects together an air cleaner provided on a side toward an intake port for introducing external air and a throttle body provided on a side toward the engine, the first pressure sensor being located on the air cleaner side of a midpoint between the air cleaner and a throttle valve provided in the throttle body, and the second pressure sensor being provided between the engine and the throttle valve;

a signal processing step, performed by a signal processing section, of changing the pressure signals in accordance with an operation state of the vehicle; and an intake sound output step, performed by a speaker disposed in the vehicle, of outputting the pressure signals processed by the signal processing section as an intake sound of the engine.

According to the vehicle sound generation method of the present invention, it is possible to generate a comfortable sound in the vehicle, the sound closely resembling the actual intake sound of the engine and being decreased in noise level.

MODE FOR CARRYING OUT THE INVENTION

First Embodiment

Figure 1:
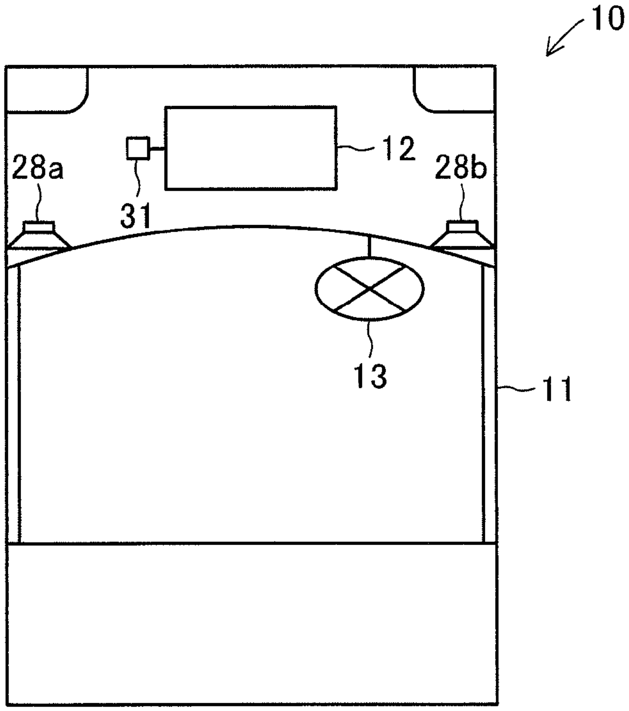
FIG. 1 Plan view schematically showing an automobile which includes a vehicle sound generation apparatus according to a first embodiment of the present invention.
Figure 2:
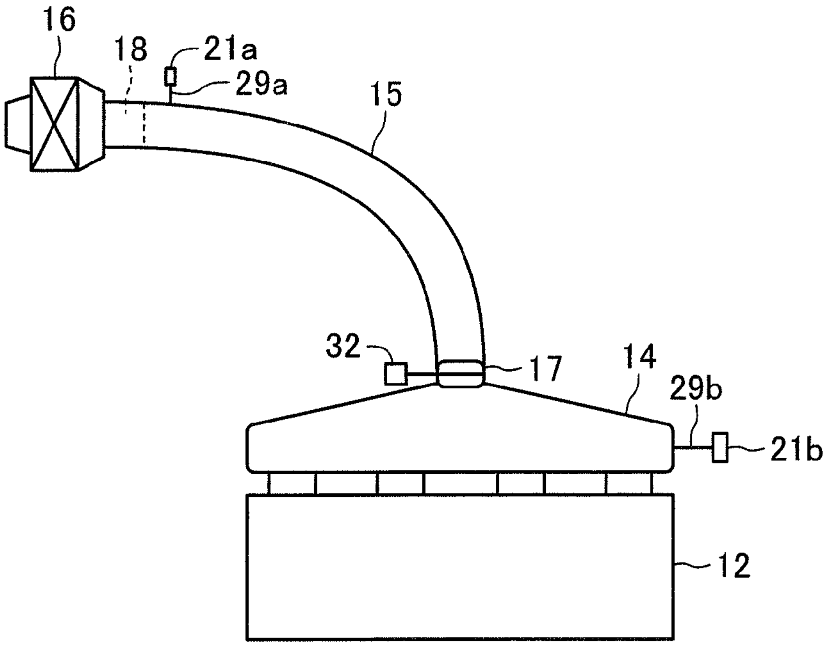
FIG. 2 Schematic view showing the positions of pressure sensors of the vehicle sound generation apparatus according to the first embodiment.

A first embodiment of the present invention will now be described with reference to the drawings. FIG. 1 schematically shows an automobile 10 including a vehicle sound generation apparatus 20 (see FIG. 3) according to the first embodiment. The automobile 10 is either an FF (front-engine front-wheel-drive) vehicle or an FR (front-engine rear-wheel-drive) vehicle in which an engine 12 is disposed at the center of the front of a vehicle body 11. The automobile 10 includes a pair of front wheels (unillustrated) provided at the left and right of the front of the vehicle body 11, a pair of rear wheels (unillustrated) at the left and right of the rear of the vehicle body 11, and a handle 13. As shown in FIG. 2, an air cleaner 16 is connected to the engine 12 via a surge tank 14 and an intake duct 15. A throttle body 17 is disposed at a connection portion between the surge tank 14 and the intake duct 15, and an air flow meter 18 is disposed at an end of the intake duct 15 where the air cleaner 16 is provided.

Fresh air is taken into the air cleaner 16 through an external air duct, and foreign substances contained in the fresh air are removed by the air cleaner 16, whereby clean air is fed to the intake duct 15. In the throttle body 17, there is provided a throttle valve which rotates around a shaft so as to open and close an air passage inside the throttle body 17, whereby the amount of air fed through the intake duct 15 to the surge tank 14 is regulated in accordance with the opening (position) of the throttle valve. The surge tank 14 temporarily stores air in order to decrease the flow rate of air, thereby supplying an equal amount of air to a plurality of cylinders of the engine 12. In the engine 12, fuel supplied from a fuel system is mixed with the air supplied from the surge tank 14, and the resultant mixture is burnt for explosion, to thereby generate driving force. The air flow meter 18 detects the flow rate of the air flowing from the air cleaner 16 to the intake duct 15.

Figure 3:
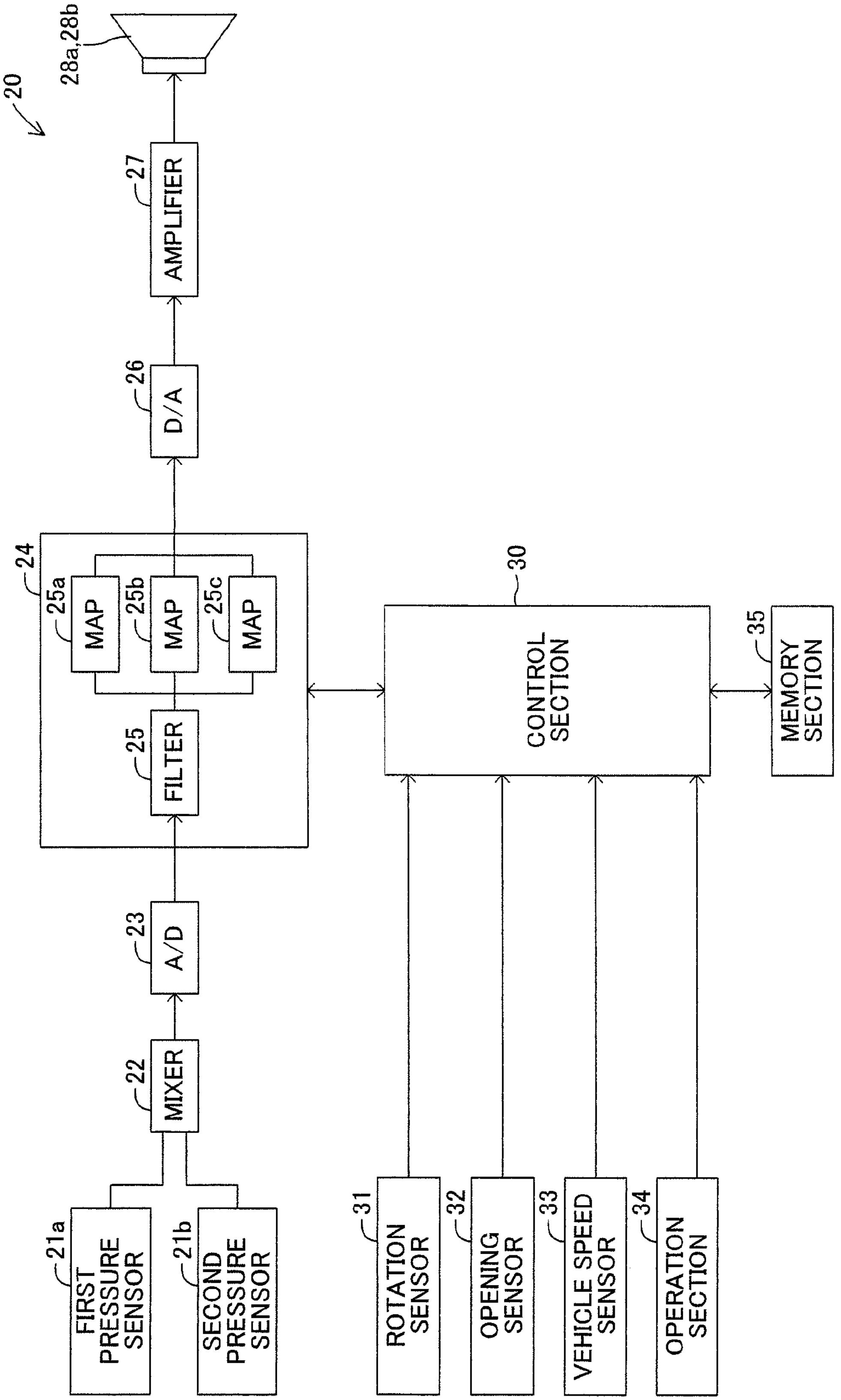
FIG. 3 Schematic diagram showing the configuration of the vehicle sound generation apparatus according to the first embodiment.
Figure 4:
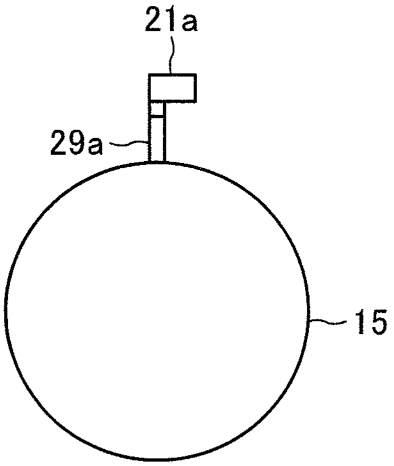
FIG. 4 Cross sectional views showing the positional relation between an intake duct and a pressure sensor, wherein (a) is an overall schematic cross sectional view, and (b) is a cross sectional view showing how the intake duct and the pressure sensor are connected together.
Figure 4:
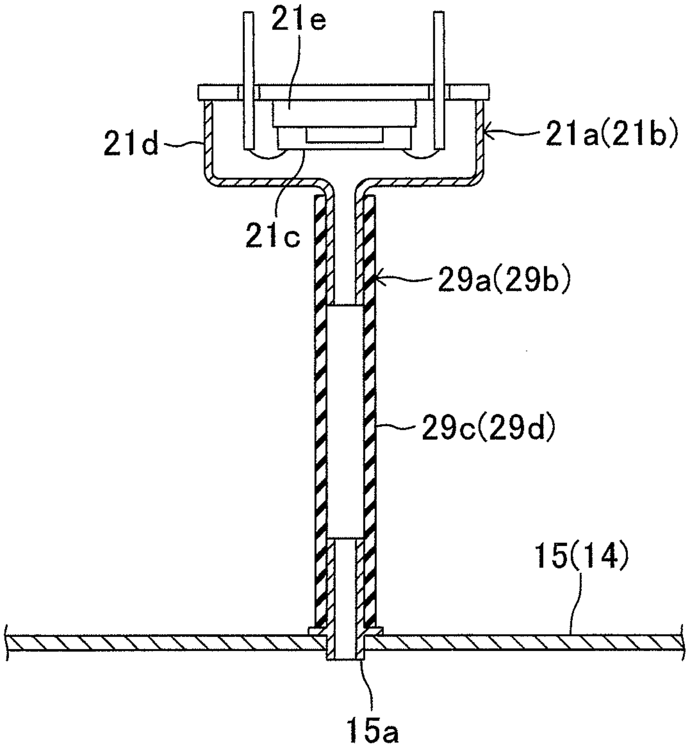

As shown in FIG. 3, the vehicle sound generation apparatus 20 includes a first pressure sensor 21*a*, a second pressure sensor 21*b*, a mixer 22, an A/D converter 23, a signal processing section 24, a D/A converter 26, an amplifier 27, and speakers 28*a* and 28*b*. A control section 30 is connected to the signal processing section 24. In addition, the vehicle sound generation apparatus 20 also includes a rotation sensor 31, an opening sensor 32, a vehicle speed sensor 33, an operation section 34, and a memory section 35 which are connected to the control section 30. The first pressure sensor 21*a* is connected to an upper portion of the circumferential wall of the intake duct 15 to be located in the vicinity of the air flow meter 18 (see FIG. 2). Specifically, as shown in FIGS. 4(*a*) and 4(*b*), the first pressure sensor 21*a* is connected to the upper portion of the circumferential wall of the intake duct 15 by use of a tube 29*c* included in a tubular communication portion 29*a*. The first pressure sensor 21*a* detects changes in pressure (intake pulsation) in the intake duct 15 and outputs the detected intake pulsation in the form of voltage change.

The tube 29*c* is a flexible resin or rubber tube whose inner diameter is 3 mm, whose outer diameter is 6 mm, and whose length is equal to or less than 4 cm. The tube 29*c* extends upward from the upper portion of the circumferential wall of the intake duct 15, and its internal space communicates with the internal space of the intake duct 15. The first pressure sensor 21*a* is attached to the upper end of the tube 29*c*. The first pressure sensor 21*a* is disposed with a pressure sensing portion 21*c* facing toward the communication portion 29*a*. The pressure sensing portion 21*c* is accommodated in a case 21*d* which closes the upper end of the tube 29*c*, and is disposed on a base 21*e* provided on an inner wall surface of the case 21*d* which is located opposite the tube 29*c*. The communication portion 29*a* is formed by the portions present between the intake duct 15 and the pressure sensing portion 21*c*. The center of a base end portion 15*a* of the communication portion 29*a* (on the intake duct 15 side) is located within a 20 cm range from the air flow meter 18.

The second pressure sensor 21*b* is installed on the outer wall surface of the surge tank 14 disposed downstream of the throttle body 17, and is composed of a sensor which is identical with the first pressure sensor 21*a*. Accordingly, in FIG. 4(*b*), a portion corresponding to the surge tank is denoted by 14, and a portion corresponding to the second pressure sensor is denoted by 21*b*. The second pressure sensor 21*b* detects the intake pulsation occurring downstream of the throttle body 17 and outputs the detected intake pulsation in the form of voltage change. The second pressure sensor 21*b* is connected to the outer wall surface of the surge tank 14 by use of a tube 29*d* (see FIG. 4(*b*) included in a communication portion 29*b*. This tube 29*d* is a flexible resin or rubber tube whose inner and outer diameters are the same as those of the tube 29*c* employed for the first pressure sensor 21*a* and whose length is equal to or less than 50 cm. Notably, the length of the communication portion 29*b* can be decreased by providing a throttle therein, and it can be rendered equal to the length of the communication portion 29*a* through proper adjustment.

Figure 5:
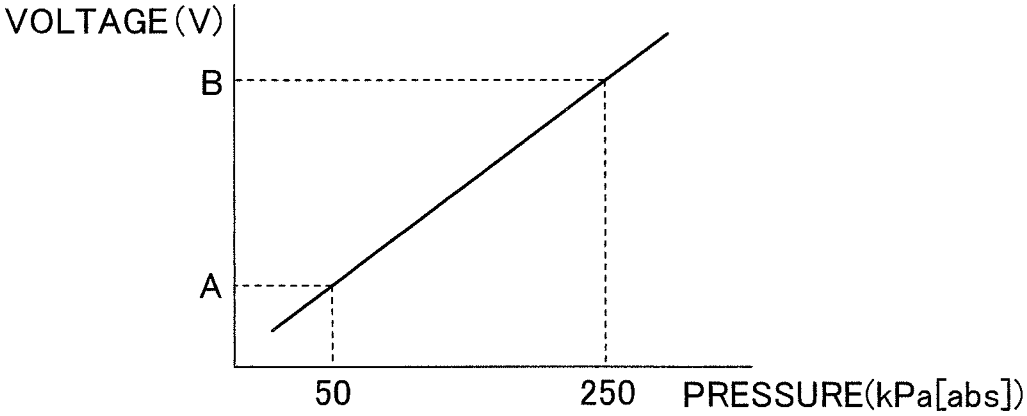
FIG. 5 Graph showing a pressure characteristic of the pressure sensor.
Figure 6:
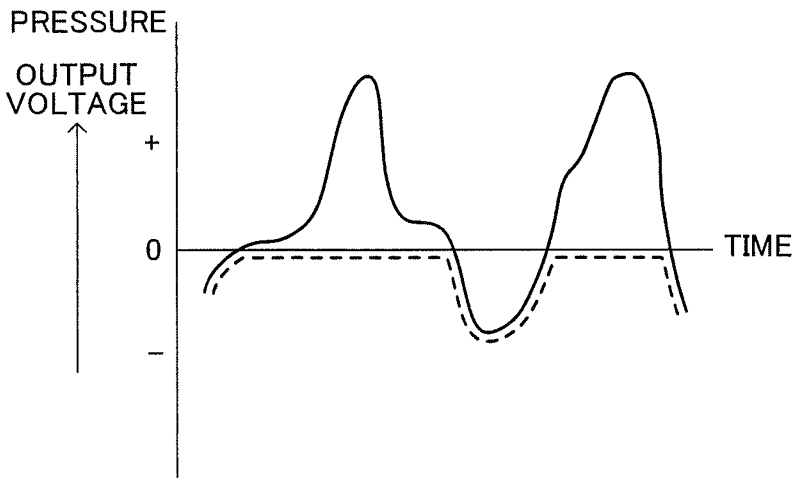
FIG. 6 Graph showing output waveforms of pressure sensors.

FIG. 5 shows the pressure characteristic of the first pressure sensor 21*a* and the second pressure sensor 21*b*. Specifically, FIG. 5 shows that each of the first pressure sensor 21*a* and the second pressure sensor 21*b* outputs a voltage which is proportional to the pressure acting thereon. The first pressure sensor 21*a* and the second pressure sensor 21*b* are designed to detect both positive and negative pressures. The solid line in FIG. 6 shows an example of an output waveform which is observed when pressure is detected by use of the first pressure sensor 21*a* or the second pressure sensor 21*b* and which shows the relation between time and the detected pressure. The broken line in FIG. 6 shows an example of an output waveform which is observed when the same pressure as that represented by the solid line is detected by use of a pressure sensor capable of detecting negative pressure only and which shows the relation between time and the detected pressure. This output waveform shows that all portions of the waveform where the pressure is equal to or higher than 0 are cut out.

The sensitivity range of the first pressure sensor 21*a* and the second pressure sensor 21*b* is from 1 Hz to 2 kHz. Notably, pressure sensors whose sensitivity range starts from 0 Hz may be used as these sensors. In this case, the DC components of the pressure signals output from the first pressure sensor 21*a* and the second pressure sensor 21*b* are removed by respective filters (unillustrated) for removing the DC components and allowing only the AC components to pass therethrough, whereby only the AC components of the pressure signals are sent to the mixer 22. The pressure signals sent to the mixer 22 are mixed together, and the resultant analog signal is converted to a digital signal by the A/D converter 23. The digital signal is sent to the signal processing section 24.

Figure 7:
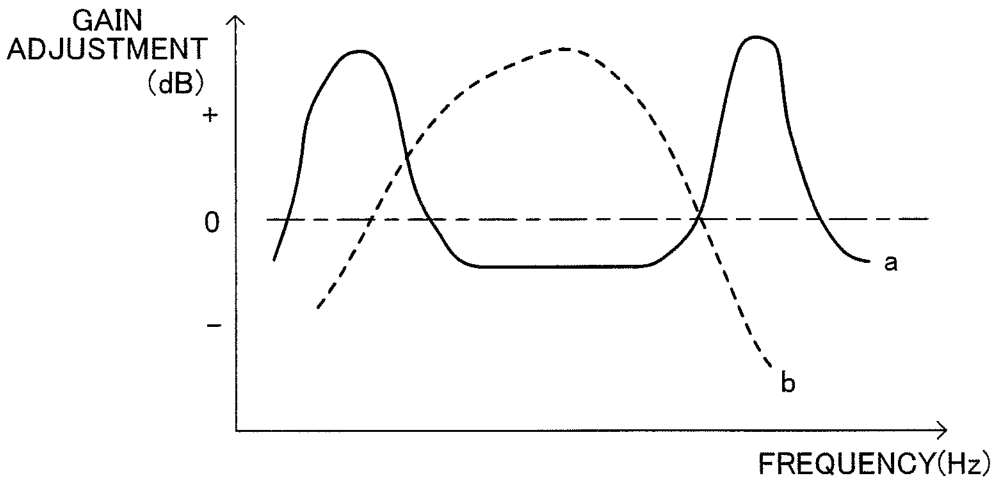
FIG. 7 Graph showing filter characteristics.

The signal processing section 24, which includes a filter 25, and maps 25*a*, 25*b*, and 25*c*, performs filtering processing on the digital signal received from the A/D converter 23 in order to change its frequency characteristic. The filter 25 is composed of a plurality of filters, for example, filters a and b whose characteristics are shown in FIG. 7. The filter a whose characteristic is represented by a solid line in FIG. 7 increases gain in low- and high-frequency ranges, and decreases gain in a range therebetween. The filter b whose characteristic is represented by a broken line in FIG. 7 decreases gain in the low- and high-frequency ranges, and increases gain in the range therebetween. Although not illustrated, the filter 25 includes filters other than the filters a and b, thereby allowing the driver to select a desired filter from thereamong.

By means of selecting either one of the filters a and b shown in FIG. 7, a sound to be produced can be changed, for example, such that a sound imitating the engine sound of a sports car is generated. The map 25*a* is employed so as to change the level of the sound pressure signal received from the A/D converter 23 and/or the gain of the filter 25 throughout the entire frequency range, and is composed of, for example, a sound pressure amplification map shown in FIG. 8. This sound pressure amplification map is employed so as to increase the levels of the output signals of the first pressure sensor 21*a* and the second pressure sensor 21*b* and/or the gain of the filter 25 throughout the entire frequency range on the basis of the rotational speed (engine speed) of the engine 12 detected by the rotation sensor 31 and the opening of the throttle valve detected by the opening sensor 32.

Figure 8:
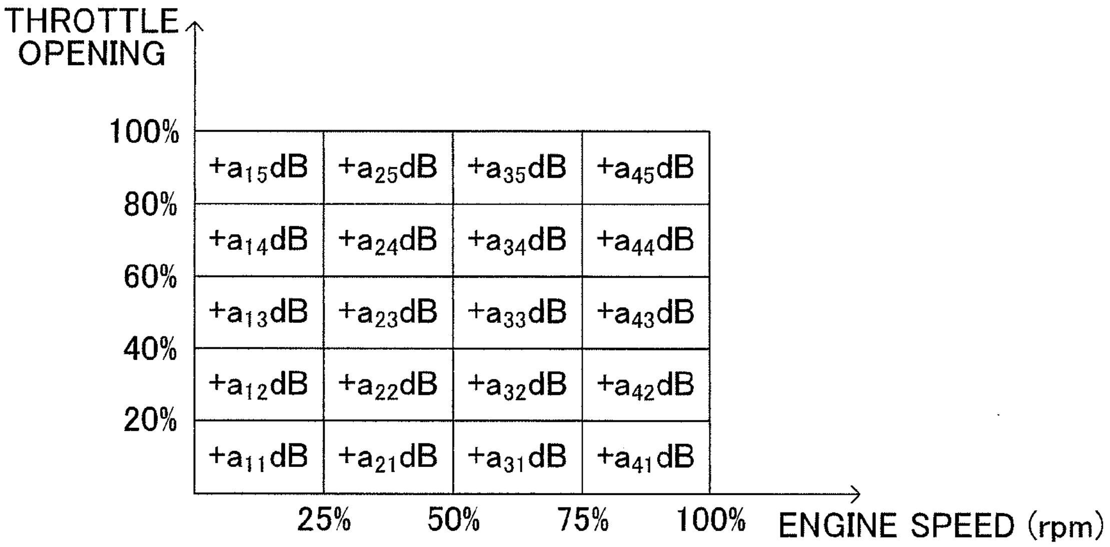
FIG. 8 Map for increasing/decreasing sound pressure in accordance with engine speed and throttle opening.

The sound pressure amplification map shown in FIG. 8 is a table prepared as follows. The range of the engine speed rpm (the horizontal axis) between the minimum value (0) and the maximum value is divided into four equal segments, and the range of the throttle opening (the vertical axis) between the minimum value (0) and the maximum value (100) is divided into five equal segments. A gain to be added is described in each of cells located at the intersections of "throttle opening" rows and "engine speed" columns. By means of obtaining different values from the map 25*a* on the basis of different combinations of the engine speed and the throttle opening and interpolating them, the levels of the output signals of the first pressure sensor 21*a* and the second pressure sensor 21*b* and/or the gain of the filter 25 can be increased throughout the entire frequency range.

Figure 9:
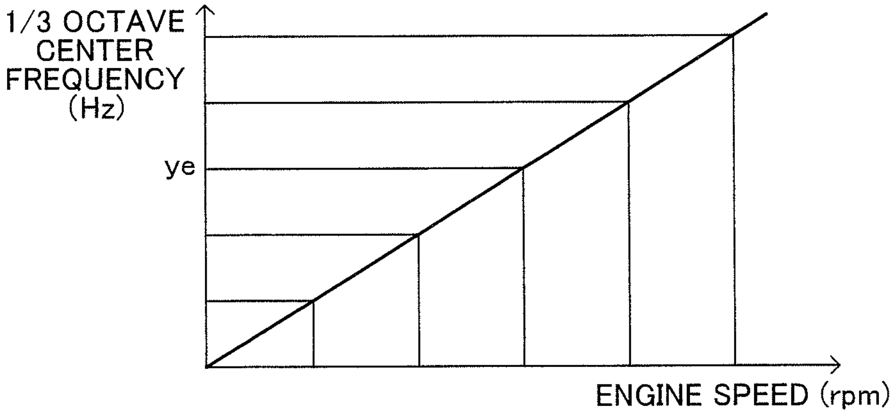
FIG. 9 Graph showing the relation between engine speed and ⅓ octave frequency.
Figure 10:
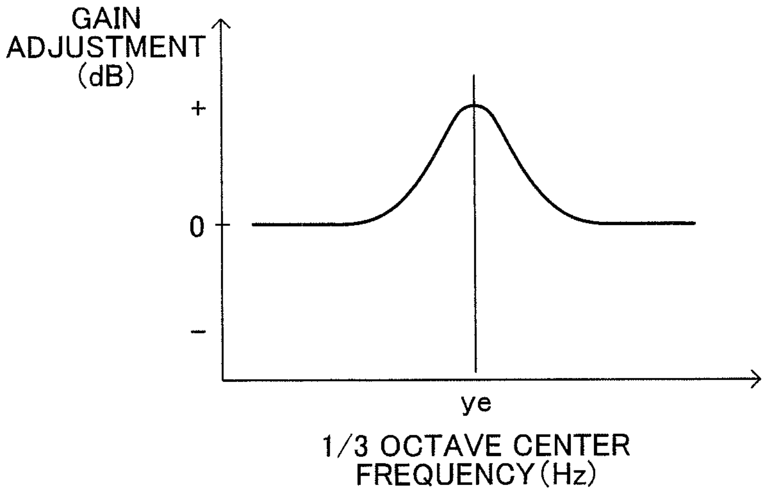
FIG. 10 Gain adjustment map showing the relation between ⅓ octave frequency and gain.

The map 25*b* is employed so as to change the level of the sound pressure signal received from the A/D converter 23 and/or the gain of the filter 25 in a portion of the entire frequency range, and is composed of a ⅓ octave center frequency graph representing the relation between the engine speed detected by the rotation sensor 31 and the ⅓ octave center frequency (see FIG. 9) and a gain adjustment graph (see FIG. 10). By use of the ⅓ octave center frequency graph shown in FIG. 9, a ⅓ octave center frequency is obtained from the engine speed detected by the rotational sensor 31. By use of the gain adjustment graph shown in FIG. 10, the value of the gain at the obtained ⅓ octave center frequency is obtained. Subsequently, the levels of the output signals of the first pressure sensor 21*a* and the second pressure sensor 21*b* and/or the gain of the filter is increased at a corresponding frequency.

Figure 11:
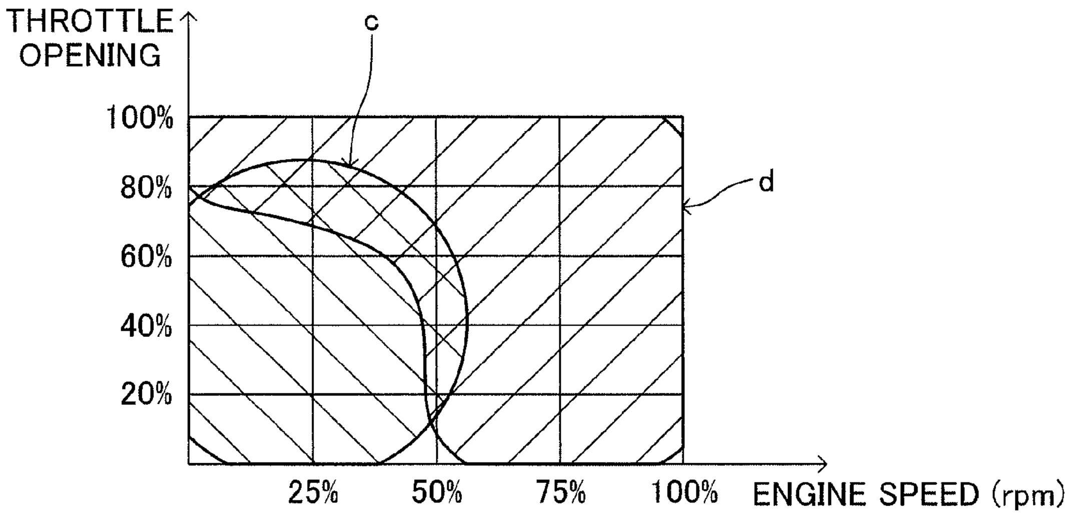
FIG. 11 Map for performing effector processing in accordance with the engine speed and the throttle opening.

The map 25*c* is employed so as to perform compressor processing and/or reverberator processing on the pressure signals output from the first pressure sensor 21*a* and the second pressure sensor 21*b*, and/or the sound pressure signal which is processed on the basis of the filter characteristic of the filter 25. The map 25*c* is composed of an effector processing map shown in FIG. 11. The effector processing map shown in FIG. 11 is a table prepared as follows. The range of the engine speed rpm (the horizontal axis) between the minimum value (0) and the maximum value is divided into four equal segments, and the range of the throttle opening (the vertical axis) between the minimum value (0) and the maximum value (100) is divided into five equal segments. Areas located at the intersections of “throttle opening” rows and “engine speed” columns are classified into two areas; i.e., an area where compressor processing is performed and an area where reverberator processing is performed. By use of this effector processing map, effector processing is performed on the sound pressure signal in accordance with the value obtained from the engine speed and the throttle opening.

In this case, in an area c shown in FIG. 11 where both the value of the engine speed detected by the rotation sensor 31 and the value of the throttle opening detected by the opening sensor 32 are small (at low-speed low-load time), compressor processing for amplifying the sound pressure signal is performed. In an area d shown in FIG. 11 where the value of the engine speed detected by the rotation sensor 31 is large (at high-speed time), the value of the throttle opening detected by the opening sensor 32 is large (at high-load time), or both of these values are large (at high-speed high-load time), reverberator processing is performed. Thus, at the low-speed low-load time, the sound pressure signal is amplified. At other times, a reverberation effect is exerted on the intake sound output from the speakers such that the occupants feel the intake sound being prolonged and continuing.

The digital signal processed by the signal processing section 24 is converted to an analog signal by the D/A converter 26, the analog signal is amplified by the amplifier 27, and the amplified signal is sent to the speakers 28*a* and 28*b*, to thereby output intake sound therefrom. The speaker 28*a* and 28*b* are separately installed at the left and right of the front of the vehicle body 11. As shown in FIG. 1, the speaker 28*a* is installed inside a glove compartment provided at the left of a dashboard which is located at the front of the vehicle body 11, and the speaker 28*b* is installed inside a wall panel provided on the right side of the dashboard. The speakers 28*a* and 28*b* are disposed in such orientation that the sound produced by each speaker propagates in a direction from the engine 12 toward the cabin.

The control section 30 is connected to the memory section 35 which stores a control program for controlling the vehicle sound generation apparatus 20 and various types of data. The control section 30 executes the control program stored in the memory section 35 on the basis of the signals received from the sensors which will be described later. The rotation sensor 31 is installed on the engine 12 in order to detect the rotational speed of the engine 12, to thereby send to the control section 30 a signal representing the detected rotational speed. The opening sensor 32 is installed on the shaft of the throttle valve in order to detect the rotational angle of the shaft as the opening of the throttle valve, to thereby send to the control section 30 a signal representing the detected throttle valve opening.

The vehicle speed sensor 33 is installed at the front of a transmission in order to detect the traveling speed of the automobile 10, to thereby send to the control section 30 a signal representing the detected traveling speed. The operation section 34 is disposed on the surface of the dashboard, and includes a selector switch, three push-button switches, and other controls. By operating the selector switch, the driver can select a desired filter from among the filters included in the filter 25. Notably, the driver can operate this selector switch such that no filter is selected. The three push-button switches correspond to the maps 25*a*, 25*b*, and 25*c*. By turning ON/OFF these switches, the driver can determine whether to perform the relevant types of processing by use of the maps 25*a*, 25*b*, and 25*c*.

The remaining controls include a main switch for turning ON/OFF the vehicle sound generation apparatus 20, a control for adjusting the overall volume of the speakers 28*a* and 28*b*, and a control for adjusting localization of sound by changing the sound balance between the sound output from the speaker 28*a* and the sound output from the speaker 28*b*. In addition, the selector switch and other controls of the operation section 34 can be remotely operated by radio. For example, various types of switching operations can be performed by use of a cellular phone. The data in the signal processing section 24 can be rewritten via a communication means such as a cellular phone.

Next, there will be described a driver's operation for operating the vehicle sound generation apparatus 20 in order to cause the speakers 28*a* and 28*b* to output the intake sound of the engine 12 during travelling of the automobile 10 configured as mentioned above, and control which is performed by the control section 30 so as to operate the vehicle sound generation apparatus 20. First, the driver operates the selector switch of the operation section 34 in order to select a desired filter from among the filters included in the filter 25, and operates the three push-button switches of the operation section 34 in order to determine whether to perform the relevant types of processing in accordance with the maps 25*a*, 25*b*, and 25*c*. In addition, setting is performed so as to render the level of the pressure signal output from the second pressure sensor 21*b* lower than the level of the pressure signal output from the first pressure sensor 21*a*.

Next, the driver sets the starting switch to the ON state in order to start the engine 12, and sets the main switch of the vehicle sound generation apparatus 20 to the ON state. Next, the driver steps on an accelerator pedal in order to cause the automobile 10 to travel. The control section 30 determines a predetermined value from each of the maps 25*a*, 25*b*, and 25*c* on the basis of the detected values received from the rotation sensor 31 and the opening sensor 32, and adds the determined predetermined value(s) to the filter that the driver has selected from among the filters included in the filter 25. Thus, the pressure signals output from the first pressure sensor 21*a* and the second pressure sensor 21*b* are processed by the signal processing section 24, whereby each of the speakers 28*a* and 28*b* produces the sound which changes in accordance with the filter characteristic used in the processing performed by the signal processing section 24.

The intake sound output from the speakers 28*a* and 28*b* changes with the pressures detected by the first pressure sensor 21*a* and the second pressure sensor 21*b*, the engine speed (the rotational speed of the engine 12) detected by the rotation sensor 31, and the throttle valve opening detected by the opening sensor 32. Notably, in the case where the selector switch of the operation section 34 is set such that none of the filters included in the filter 25 is selected and all the three push-button switches of the operation section 34 are set to the OFF state, the sound pressure signal is not processed, whereby intake sound is output from the speakers 28*a* and 28*b* on the basis of the pressure signals output from the first pressure sensor 21*a* and the second pressure sensor 21*b*. Notably, in a state in which all the windows of the automobile 10 are closed, the intake sound output from the speakers 28*a* and 28*b* hardly leaks out of the automobile 10, and can be heard only by the occupants in the cabin.

As mentioned above, in the vehicle sound generation apparatus 20 according to the present embodiment, the first pressure sensor 21*a* is provided on the intake duct 15 to be located in the vicinity of the air flow meter 18, and the second pressure sensor 21*b* is provided on the outer wall surface of the surge tank 14. By virtue of this, not only intake pulsation occurring upstream of the throttle body 17 but also intake pulsation occurring downstream thereof can be detected. As a result, the intake sound output from the speakers 28*a* and 28*b* can change with not only the quantity of the air passing through the air cleaner 16 but also the pulsation occurring due to operation of the engine 12.

During normal traveling of the automobile 10, the speakers 28*a* and 28*b* output a sound which is produced on the basis of the pressure signal obtained by mixing the pressure signal output from the second pressure sensor 21*b* and the pressure signal output from the first pressure sensor 21*a*. In contrast, when the automobile 10 is decelerating, idling, or under low load, the speakers 28*a* and 28*b* output a sound which is produced on the basis of mainly the pressure signal output from the second pressure sensor 21*b*. Thus, the intake sound output from the speakers 28*a* and 28*b* is rendered similar to the actual intake sound of the engine 12. As described above, even when the throttle valve in the throttle body 17 is closed (e.g., when the automobile is decelerating, idling, or under low load), the speakers 28*a* and 28*b* can output the sound which is produced on the basis of the pulsation of the engine 12.

Notably, the distance between the air flow meter 18 and the center of the base end portion 15*a* of the communication portion 29*a*, which connects the first pressure sensor 21*a* to the intake duct 15, was determined through an experiment. Preferably, this distance is equal to or less than 20 cm. In this experiment, in the case where the length of the intake duct 15 was set to the minimum length of 40 cm, an good result was obtained when the distance between the air flow meter 18 and the center of the base end portion 15*a* of the communication portion 29*a* was set to 20 cm or less. In the case where the length of the intake duct 15 is 40 cm or more, the distance between the air flow meter 18 and the center of the base end portion 15*a* of the communication portion 29*a* may be increased to 20 cm or more. Even in this case, a good result was obtained by connecting the communication portion 29*a* to a portion of the intake duct 15 which is closer to the air flow meter 18 in relation to the center of the intake duct 15.

In the present embodiment, pressure sensors whose sensitivity range is 1 Hz to 2 kHz are employed as the first pressure sensor 21*a* and second pressure sensor 21*b*. The first pressure sensor 21*a* is connected to an upper portion of the circumferential wall of the intake duct 15 by use of the tube 29*c*, and the length of the communication portion 29*a* is set to 4 cm or less. The second pressure sensor 21*b* is connected to the outer wall surface of the surge tank 14 by use of the tube 29*d*, and the length of the communication portion 29*b* is set to 50 cm or less. Thus, by means of using the first pressure sensor 21*a* and the second pressure sensor 21*b* whose sensitivity range is 1 Hz to 2 kHz, the speakers 28*a* and 28*b* can output only the sound that the occupants feel comfortable without outputting the sound that the occupants feel uncomfortable.

In addition, by means of setting the length of the communication portion 29*a* to 4 cm or less, resonance can be prevented from occurring inside the communication portion 29*a*. That is, in a tubular body like the communication portion 29*a* whose base end portion 15*a* (on the intake duct 15 side) is open and whose distal end is closed by the first pressure sensor 21*a*, resonance occurs when the length of the tubular body is ¼ of the wavelength or longer. Therefore, by means of setting the length of the communication portion 29*a* to less than 4 cm, it can be rendered shorter than ¼ of the wavelength of a sound wave having a required frequency. Thus, resonance can be prevented from occurring. In addition, by means of indirectly connecting the first pressure sensor 21*a* to the intake duct 15 by use of the communication portion 29*a*, an adverse effect can be prevented from being exerted on detection of the intake air pressure by the first pressure sensor 21*a*.

Meanwhile, since the second pressure sensor 21*b* is located in the vicinity of the engine 12, the second pressure sensor 21*b* is likely to pick up (detect) rough sound generated due to pulsation of the engine 12. To solve this problem, the length of the communication portion 29*b* between the outer wall surface of the surge tank 14 and the pressure sensing portion of the second pressure sensor 21*b* is increased to 50 cm so as to abate the rough sound generated due to pulsation of the engine 12. The results of an experiment show that a good result can be obtained when the length of the communication portion 29*b* is between 4 cm and 50 cm. In addition, since the communication portion 29*a* extends upward from the upper portion of the circumferential wall of the intake duct 15, oil accumulated inside the intake duct 15 can be prevented from flowing toward the first pressure sensor 21*a*. In addition, since the first pressure sensor 21*a* and the second pressure sensor 21*b* can measure both positive and negative pressures, all intake pulsations can be detected without fail.

In the present embodiment, since signal processing can be performed by use of the filter characteristics of the filter 25, gain can be arbitrarily changed at different frequencies. In addition, since the filter 25 has a plurality of filter characteristics, various kinds of sound can be output from the speakers 28*a* and 28*b*. In addition, by means of using the sound pressure amplification map (map 25*a*) for the signal processing performed by the signal processing section 24, the levels of the pressure signals output from the first pressure sensor 21*a* and the second pressure sensor 21*b* and/or the gain of the filter 25 can be increased throughout the entire frequency range. By virtue of this, the speakers 28*a* and 28*b* can reproduce in the cabin the intake sound whose attenuation characteristic and transmission loss are similar to those of the actual intake sound of the engine 12.

In addition, by means of using the gain adjustment map (map 25*b*) for the signal processing performed by the signal processing section 24, the sound pressure signal can be enhanced in accordance with an order component (a frequency component) determined from the engine speed. In addition, by means of using the effector processing map (map 25*c*) for the signal processing performed by the signal processing section 24, compressor processing can be performed when both the value of the engine speed and the value of the throttle opening are small (at low-speed low-load time), and reverberator processing can be performed when the value of the engine speed is large (at high-speed time), the value of the throttle opening is large (at high-load time), or both of these values are large (at high-speed high-load time).

As mentioned above, by means of performing the compressor processing or the reverberator processing in accordance with the operation state of the automobile 10, the sound pressure can be enhanced or a reverberation effect can be exerted on the intake sound output from the speakers 28*a* and 28*b* such that the occupants feel the intake sound being prolonged and continuing. In addition, since the speakers 28*a* and 28*b* are separately disposed at the left and right of the dashboard which is provided at the front of the vehicle body 11 such that the sound produced by each speaker propagates in a direction from the engine 12 to the cabin, the occupants can feel that the intake sound output from the speakers 28*a* and 28*b* comes from the engine 12. As a result, the occupants can feel this sound to be the actual intake sound of the engine 12.

Second Embodiment

Figure 12:
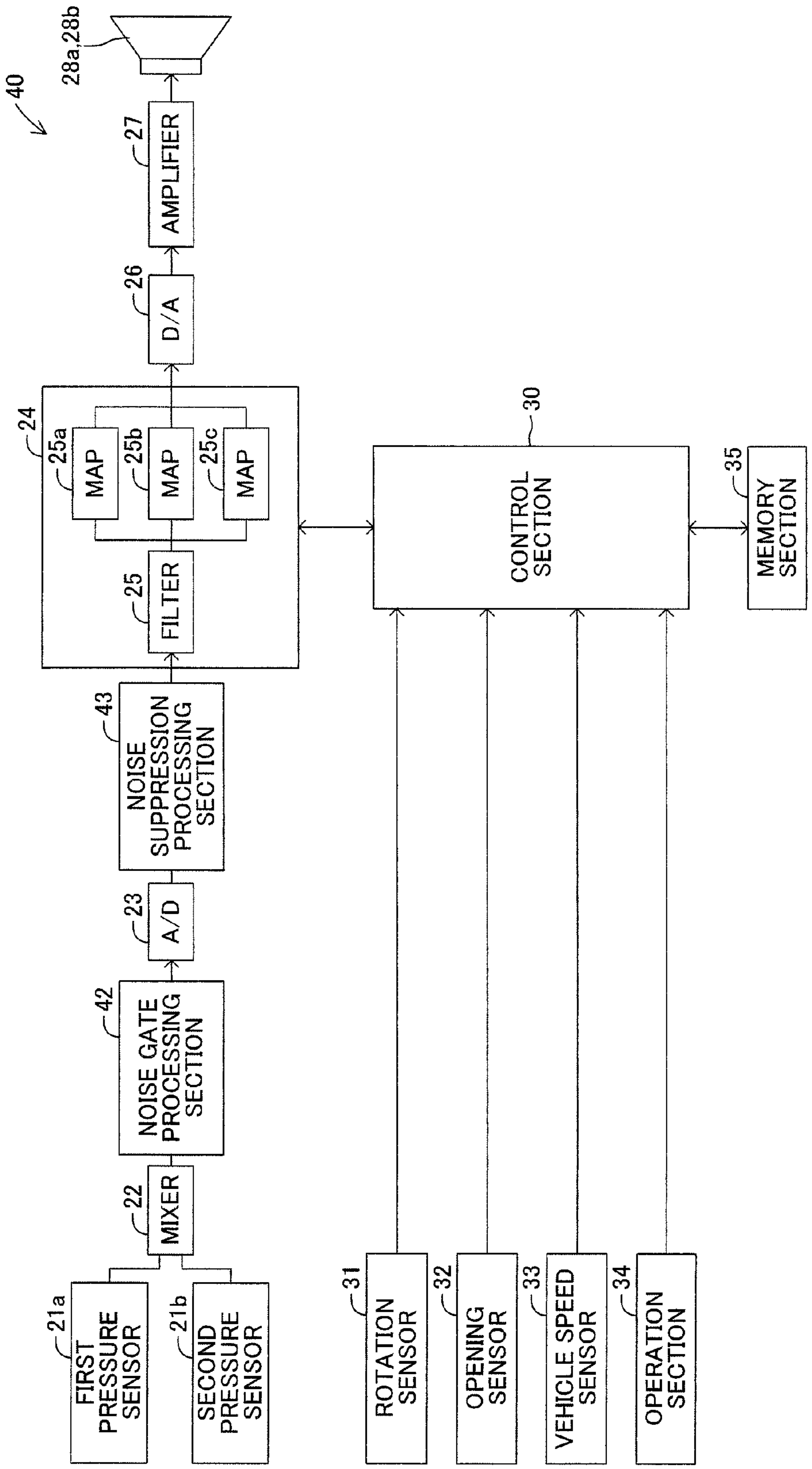
FIG. 12 Schematic diagram showing the configuration of a vehicle sound generation apparatus according to a second embodiment of the present invention.

FIG. 12 shows a vehicle sound generation apparatus 40 according to a second embodiment of the present invention. The vehicle sound generation apparatus 40 includes a noise gate processing section 42 and a noise suppression processing section 43. The remaining components of the vehicle sound generation apparatus 40 are the same as those of the above-described vehicle sound generation apparatus 20. Accordingly, in FIG. 12, these components are identified by the same symbols as those used to identify the corresponding components of the vehicle sound generation apparatus 20. The noise gate processing section 42 performs noise gate processing on the sound pressure signal output from the mixer 22. The purpose of the noise gate processing is to reduce noise. Specifically, in the case where the level of the input signal is lower than a predetermined threshold level, the gain of the frequency spectrum is decreased in order to close the gate. In contrast, in the case where the level of the input signal is equal to or higher than the threshold level, the gate is opened so as to send the input signal to the A/D converter 23. Namely, the noise gate processing section 42 performs processing in which sound whose level is lower than a predetermined level is removed as noise. The electrical signal sent to the A/D converter 23 converter is converted to a digital signal therein, and the digital signal is sent to the noise suppression processing section 43. Notably, the noise gate processing may be performed on the digital signal.

The noise suppression processing section 43 performs noise suppression processing on the electrical signal converted to the digital signal by the A/D converter 23. In this noise suppression processing, the electrical signal is processed through use of an FFT (Fast Fourier Transform) algorithm. Specifically, data representing the signal received from the A/D converter 23 and data representing the noise appearing at predetermined intervals are Fourier-transformed in order to obtain their transformed values. The transformed value of the noise data is subtracted from the transformed value of the signal data, and then the resultant value is inversely transformed to the original signal data, to thereby remove noise. In this case, a signal in the time domain is transformed to a signal in the frequency domain, noise contained in this signal is estimated, the noise is removed from the signal in the frequency domain, and then the signal in the frequency domain is inversely transformed to a signal in the time domain. By means of performing the above-mentioned so-called spectral subtraction processing, a noise-free electrical signal can be obtained. This electrical signal is sent to the signal processing section 24. Notably, needless to say, noise suppression processing other than the spectral subtraction processing may be used.

All components of the vehicle sound generation apparatus 40 other than the noise gate processing section 42 and the noise suppression processing section 43 have the same functions as those of the corresponding components of the above-described vehicle sound generation apparatus 20. The vehicle sound generation apparatus 40 configured as mentioned above can remove or suppress the noise in an unnecessary frequency range, which is contained in the intake sound output from the speakers 28*a* and 28*b*, to thereby generate natural intake sound. The remaining actions and effects of the vehicle sound generation apparatus 40 are the same as those of the above-described vehicle sound generation apparatus 20. Notably, in the above-described second embodiment, both the noise gate processing section 42 and the noise suppression processing section 43 are included in the vehicle sound generation apparatus 40; however, either one of these components may be omitted. In addition, the noise gate processing and/or the noise suppression processing may be performed on either an analog signal or a digital signal.

Third Embodiment

Figure 13:
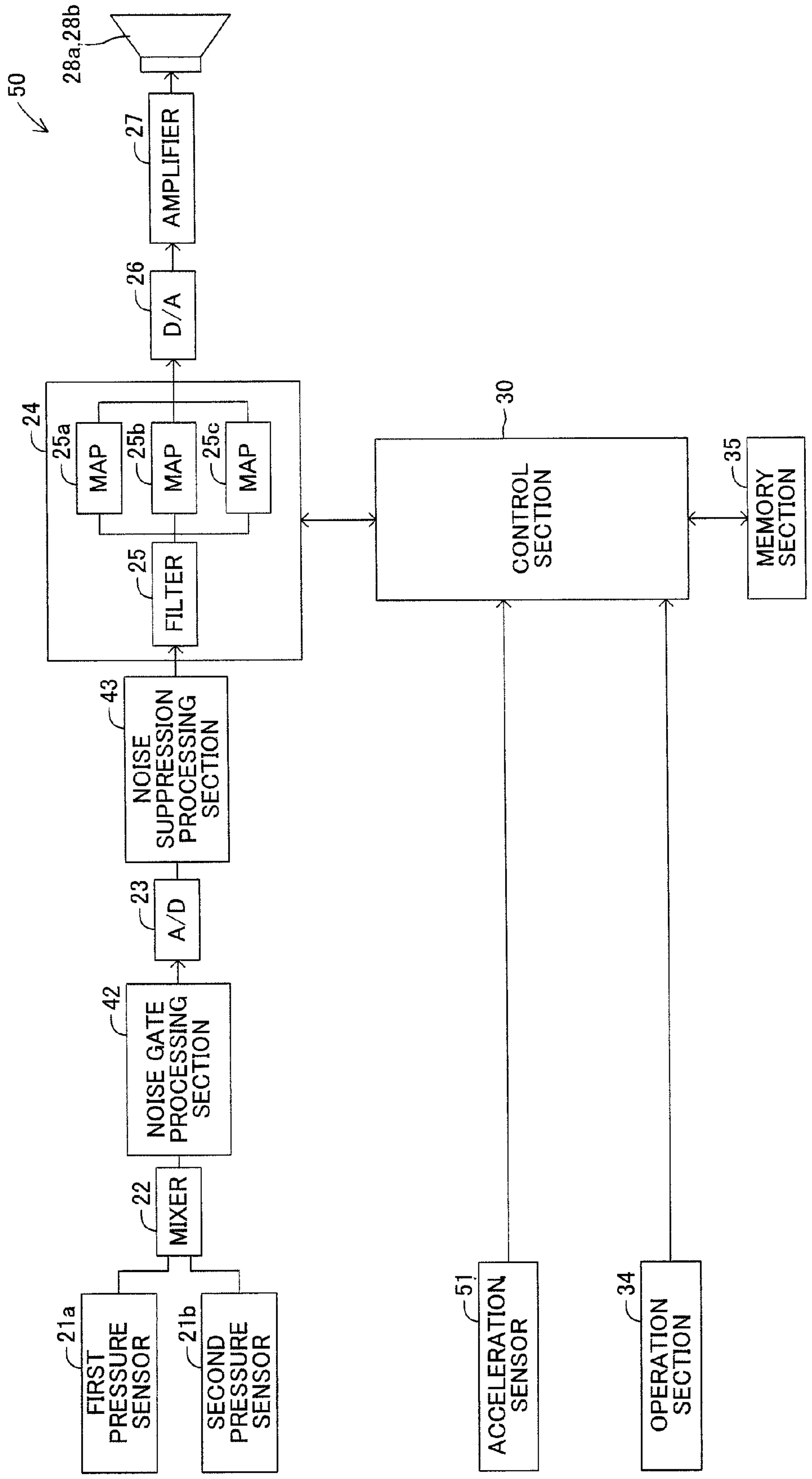
FIG. 13 Schematic diagram showing the configuration of a vehicle sound generation apparatus according to a third embodiment of the present invention.

FIG. 13 shows a vehicle sound generation apparatus 50 according to a third embodiment of the present invention. The vehicle sound generation apparatus 50 includes an acceleration sensor 51 in place of the rotation sensor 31, the opening sensor 32, and the vehicle speed sensor 33 included in the above-described vehicle sound generation apparatus 40. The acceleration sensor 51 may be installed, for example, at the center of the bottom of the vehicle body 11 of the automobile 10 shown in FIG. 1. The remaining components of the vehicle sound generation apparatus 50 are the same as those of the above-described vehicle sound generation apparatus 40. Accordingly, these components are identified by the same symbols as those used to identify the corresponding components of the vehicle sound generation apparatus 40, and specific descriptions thereof are omitted.

Since the vehicle sound generation apparatus 50 includes the acceleration sensor 51 as mentioned above, the control section 30 can perform sound pressure amplification processing on the pressure signals output from the first pressure sensor 21*a* and the second pressure sensor 21*b*, or increase the gain of the filter for processing the pressure signals output from the first pressure sensor 21*a* and the second pressure sensor 21*b* throughout the entire frequency range, on the basis of the value of acceleration detected by the acceleration sensor 51. In this case, in accordance with acceleration of the automobile 10, the filter 25, the map 25*a*, and so on are used to determine the frequency range where gain is to be increased or decreased, and/or to increase the levels of the output signals of the first pressure sensor 21*a* and the second pressure sensor 21*b* and the gain of the filter 25 throughout the entire frequency range. In addition, since the acceleration sensor 51 can be installed at an arbitrary position in the vehicle, neither modification of the automobile 10 nor complicated wiring is required, thereby facilitating installation thereof. The remaining actions and effects of the vehicle sound generation apparatus 50 are the same as those of the above-described vehicle sound generation apparatus 40.

Fourth Embodiment

Figure 14:
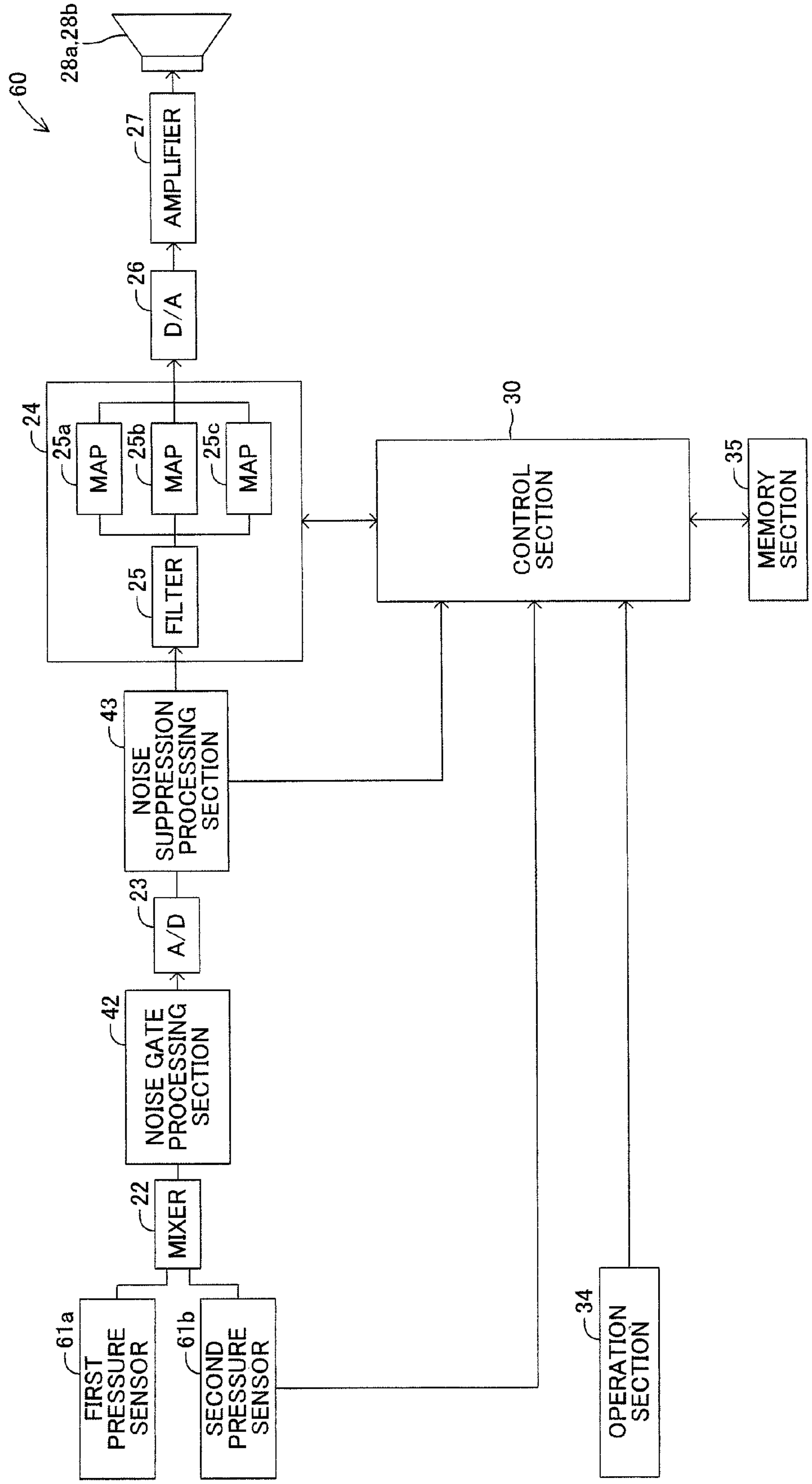
FIG. 14 Schematic diagram showing the configuration of a vehicle sound generation apparatus according to a fourth embodiment of the present invention.

FIG. 14 shows a vehicle sound generation apparatus 60 of a fourth embodiment of the present invention. The vehicle sound generation apparatus 60 includes a first pressure sensor 61*a* and a second pressure sensor 61*b*, but does not include the rotation sensor 31, the opening sensor 32, and the vehicle speed sensor 33 included in the vehicle sound generation apparatus 40 according to the above-described second embodiment. The second pressure sensor 61*b* is connected not only to the mixer 22 but also to the control section 30. The remaining components of the vehicle sound generation apparatus 60 are the same as those of the vehicle sound generation apparatus 40. Accordingly, these components are identified by the same symbols as those used to identify the corresponding components of the vehicle sound generation apparatus 40, and specific descriptions thereof are omitted.

In the present embodiment, by means of connecting the second pressure sensor 61*b* to the control section 30 via the noise gate processing section 42, the A/D converter 23, the noise suppression processing section 43, and so on, an AC component signal can be sent to the control section 30, whereby the control section 30 can recognize the rotational speed of the engine 12. In addition, by means of directly connecting the second pressure sensor 61*b* to the control section 30, a DC component signal can be sent to the control section 30, whereby the control section can recognize the load acting on the engine 12. In this case, a portion of the pressure signal output from the second pressure sensor 61*b* is passed through a filter (unillustrated) for removing the DC component and allowing only AC components to pass therethrough. As a result, the DC component is removed, and only the AC components are sent to the mixer 22. The remaining portion of the pressure signal output from the second pressure sensor 61*b* is passed through a filter (unillustrated) for removing the AC components and allowing only the DC component to pass therethrough. As a result, the AC components are removed, and only the DC component is sent to the control section 30.

The AC component signal is subjected to noise suppression processing in the noise suppression control section 43, thereby becoming a signal which allows the control section 30 to recognize the rotational speed of the engine 12. In this case, since the frequency range where noise exists is removed and only the frequency range where intake sound exists remains, whereby the control section 30 can recognize the rotational speed of the engine 12 more reliably. Meanwhile, the DC component signal is sent directly to the control section 30, thereby becoming a signal which allows the control section 30 to recognize the load acting on the engine 12. By means of determining the operation state of the engine 12 from the above-described information (signals), the control section 30 can increase or decrease the sound pressure appropriately. In this case, the filter 25, the map 25*a*, and so on are used to determine the frequency ranges where gain is to be increased or decreased, and/or to increase the gain of the filter 25 throughout the entire frequency range in accordance with the output signals of the first pressure sensor 61*a* and the second pressure sensor 61*b*.

The vehicle sound generation apparatus 60 requires less sensors, thereby becoming simpler in configuration and cheaper. The remaining actions and effects of the vehicle sound generation apparatus 60 are the same as those of the vehicle sound generation apparatus 40 according to the above-described second embodiment. Notably, in modifications of the fourth embodiment, the vehicle sound generation apparatus 60 may include the rotation sensor 31, the opening sensor 32, and the vehicle speed sensor 33 included in the vehicle sound generation apparatus 40 according to the second embodiment; or the acceleration sensor 51 included in the vehicle sound generation apparatus 50 according to the third embodiment.

Fifth Embodiment

Figure 15:
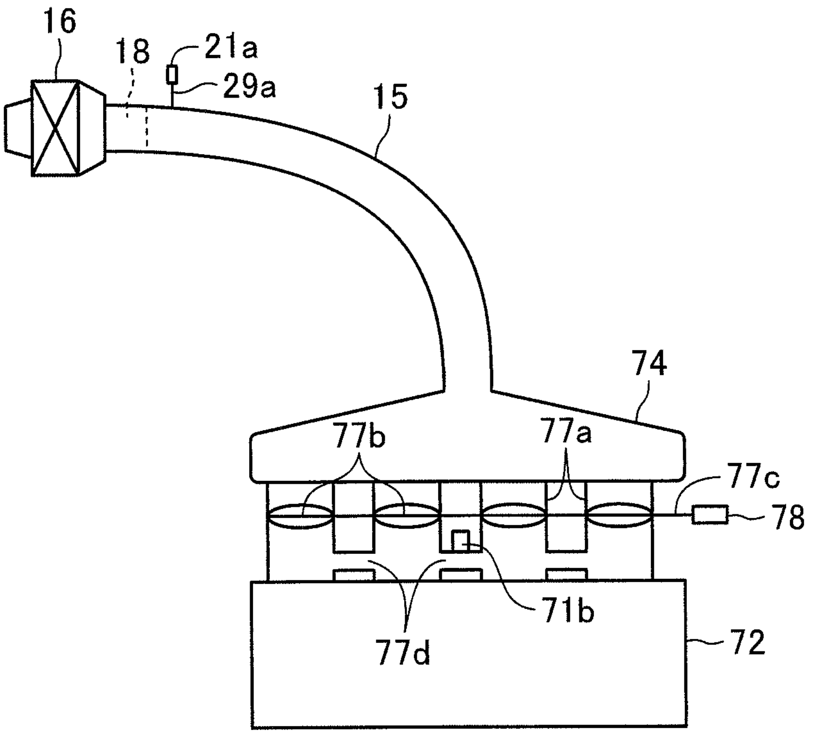
FIG. 15 Schematic view showing the positions of pressure sensors of a vehicle sound generation apparatus according to a fifth embodiment of the present invention.

FIG. 15 is a schematic view showing the position of a second pressure sensor 71*b* included in the vehicle sound generation apparatus according to a fifth embodiment of the present invention. In the present embodiment, a plurality of (four) throttle bodies 77*a*, which constitute the throttle valve according to the present invention, are disposed between an engine 72 and a surge tank 74, and no throttle body is disposed upstream of the surge tank 74. The four throttle bodies 77*a* are of an independent throttle type, and form a unit. A throttle valve 77*b* is provided in each of the throttle bodies 77*a*. The four throttle valves are operated, in synchronism with each other, by use of a single motor (unillustrated) and a single throttle shaft 77*c*. Internal spaces of the throttle bodies 77*a* communicate with each other via a balance pipe portion 77*d* provided downstream of the throttle valves 77*b*. A second pressure sensor 71*d* is disposed on the balance pipe portion 77*d*.

At the end of the throttle shaft 77*c*, there is provided an opening sensor 78 for detecting the opening of the throttle valves 77*b*. The remaining components of the vehicle sound generation apparatus according to the fifth embodiment and the automobile including the vehicle sound generation apparatus are the same as those of the above-described first embodiment. Accordingly, these components are identified by the same symbols as those used to identify the corresponding components of the first embodiment, and specific descriptions thereof are omitted.

Even in the case of the automobile having independent throttle bodies 77, the apparatus according to the present embodiment allows the occupants in the cabin to clearly hear the intake sound of the engine 72 produced in accordance with the operation state which changes as a result of the operation performed by the driver, while radiating the intake sound to the outside of the vehicle at a low level. In addition, by means of providing the second pressure sensor 71*b* on the balance pipe portion 77*d*, there can be detected pulsating components of all cylinders connected together via the balance pipe portion 77*d* of the engine 72. The remaining actions and effects of the vehicle sound generation apparatus according to the fifth embodiment are the same as those of the vehicle sound generation apparatus 20 according the first embodiment.

Notably, in a modification of the fifth embodiment, the vehicle sound generation apparatus may include the noise gate processing section 42 and the noise suppression processing section 43 which are included in the vehicle sound generation apparatus 40 of the second embodiment. In other modifications, the vehicle sound generation apparatus may include the acceleration sensor 51 included in the vehicle sound generation apparatus 50 according to the third embodiment in place or the rotation sensor 31, the opening sensor 32, and the vehicle speed sensor 33, or may be configured such that, just like in the fourth embodiment, the second pressure sensor 71*b* is connected to the mixer 22 and the control section 30 without providing the rotation sensor 31, the opening sensor 32, and the vehicle speed sensor 33. According to these modifications, the actions and effects of the vehicle sound generation apparatus according to one of the second to fourth embodiments are added to those of the vehicle sound generation apparatus according to the fifth embodiment.

Sixth Embodiment

Figure 16:
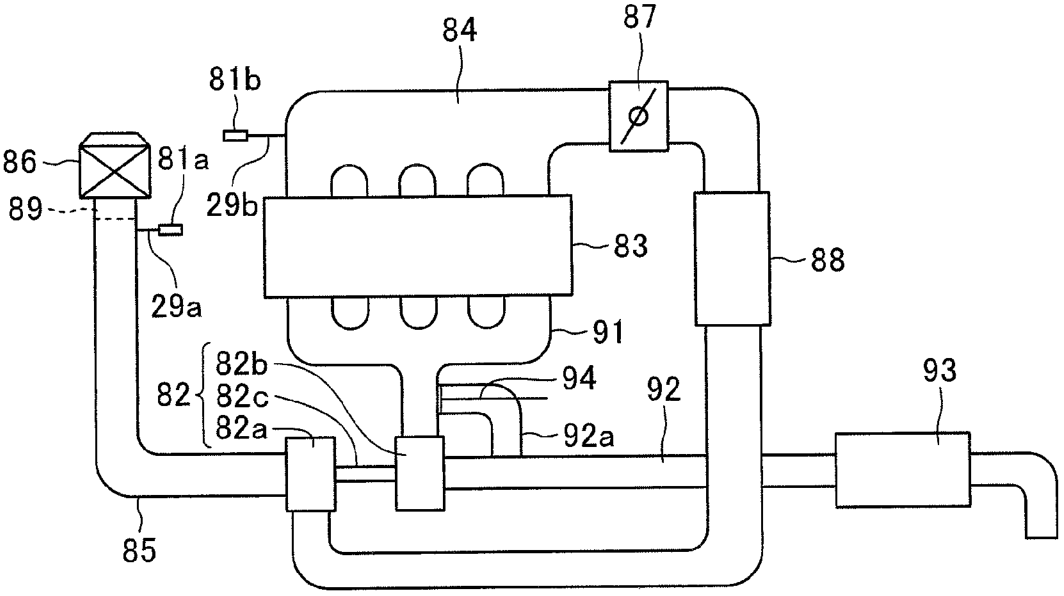
FIG. 16 Schematic view showing the positions of pressure sensors of a vehicle sound generation apparatus according to a sixth embodiment of the present invention.

FIG. 16 is a schematic view showing the positions of a first pressure sensor 81*a* and a second pressure sensor 81*b* included in the vehicle sound generation apparatus according to a sixth embodiment of the present invention. The vehicle on which the vehicle sound generation apparatus according to the present embodiment is mounted includes a turbo charger 82 which includes a compressor 82*a* and a turbine 82*b*. An air cleaner 86 is connected to an engine 83 via an intake manifold 84 and an intake duct 85. A throttle body 87 is disposed at a connection portion between the intake manifold 84 and the intake duct 85. An intercooler 88 and the compressor 82*a* are disposed in the middle of the intake duct 85. An air flow meter 89 is disposed at an end of the intake duct 85 where the air cleaner 86 is provided.

An exhaust duct 92 is connected to the exhaust side of the engine 83 via the exhaust manifold 91. The turbine 82*b* is disposed upstream of the exhaust duct 92, and a catalyst 93 is disposed downstream thereof. A part of the exhaust duct 92 located upstream of the turbine 82*b* is connected to a part of the exhaust duct 92 located downstream of the turbine 82*b* via a bypass 92*a*. A waste gate 94 is provided in the bypass 92*a*. The compressor 82*a* provided in the intake duct 85 and the turbine 82*b* provided in the exhaust duct 92 are connected together via a connecting shaft 82*c*, to thereby constituting the turbo charger 82.

The compressor 82*a* compresses the air that has passed through the air cleaner 86, and feeds the compressed air to the intercooler 88. The intercooler 88 cools the air that has become hot while passing through the compressor 82*a*, to thereby increase the density of air. The air that has passed through the intercooler 88 is fed to the engine 83 via the throttle body 87 and the intake manifold 84. Meanwhile, exhaust gas generated as a result of combustion of an air-fuel mixture within the engine 83 is fed to the turbine 82*b* via the exhaust manifold 91. This exhaust gas causes the turbine 82*b* to rotate, thereby allowing the compressor 82*a* to supply more air to the engine 83.

The waste gate 94 is employed to control rotation of the turbine 82*b*. Specifically, the waste gate 94 allows part of exhaust gas to flow into the bypass 92*a* as required, to thereby prevent exhaust gas from being fed to the turbine 82*b* excessively. The catalyst 93 removes harmful components contained in exhaust gas through reduction and oxidation. The purified exhaust gas is discharged out of the downstream end of the exhaust duct 92. The remaining components of the vehicle sound generation apparatus according to the sixth embodiment and the automobile in which the vehicle sound generation apparatus is installed are the same as those of the above-described first embodiment.

Even in the case of the automobile having the turbocharger 82, the apparatus according to the present embodiment allows the occupants in the cabin to clearly hear the intake sound of the engine 83 produced in accordance with the operation state which changes as a result of the operation performed by the driver, while radiating the intake sound to the outside of the vehicle at a low level. The first pressure sensor 81*a* may be disposed on a side of the intake duct 85 where the compressor 82*a* is provided. Even in this case, the first pressure sensor 81*a* is disposed on the intake duct 85 at a position closer to the air cleaner 86 in relation to the midpoint of the intake duct 85, which is located between the air cleaner 86 and the throttle body 87.

Thus, the first pressure sensor 81*a* can effectively detect the pressure change of intake pulsation without being influenced by the sound coming from outside the vehicle and the operating sound of the engine. Meanwhile, the operating sound of the engine is detected by the second pressure sensor 81*b*. Thus, the sound heard by the occupants in the cabin becomes similar to the actual intake sound of the engine. In this case, since the turbo charger 82 is provided, the produced intake sound of the engine becomes more powerful. The remaining actions and effects of the vehicle sound generation apparatus according to the sixth embodiment are the same as those of the vehicle sound generation apparatus according to the first embodiment.

Notably, in a modification of the sixth embodiment, the vehicle sound generation apparatus may include the noise gate processing section 42 and the noise suppression processing section 43 which are included in the vehicle sound generation apparatus according to the second embodiment. In other modifications, the vehicle sound generation apparatus may include the acceleration sensor 51 included in the vehicle sound generation apparatus 50 according to the third embodiment in place of the rotation sensor 31, the opening sensor 32, and the vehicle speed sensor 33, or may be configured such that, just like in the fourth embodiment, the second pressure sensor 71*b* is connected to the mixer 22 and the control section 30 without providing the rotation sensor 31, the opening sensor 32, and the vehicle speed sensor 33. According to the above-described modifications, the actions and effects of the vehicle sound generation apparatus according to one of the second to fourth embodiments are added to those of the vehicle sound generation apparatus according to the sixth embodiment.

Figure 17:
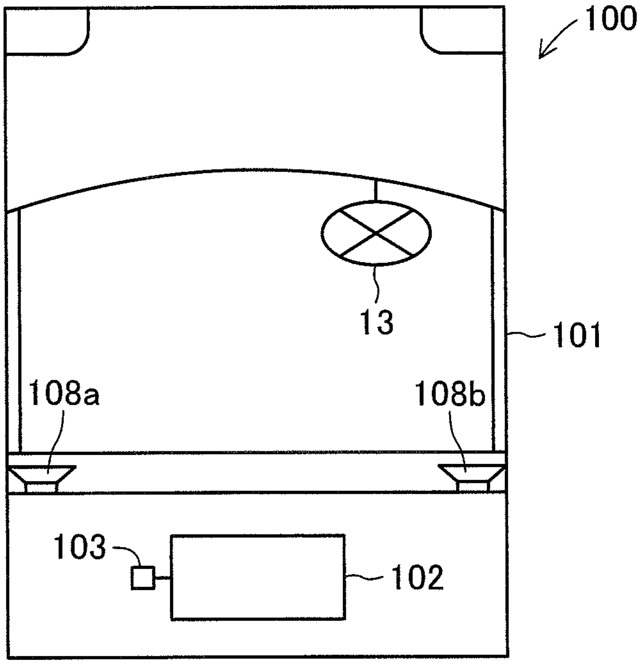
FIG. 17 Plan view schematically showing an automobile whose engine is disposed at the rear thereof.

The vehicle sound generation apparatus according to the present invention is not limited to the above-described embodiments, and may be changed freely. For example, in the above-described embodiments, the automobile 10 is an FF or FR vehicle; however, an automobile 100, which is an MR (midship engine, rear-wheel-drive) vehicle or an RR (rear-engine, rear-wheel-drive) vehicle shown in FIG. 17, may be employed in place of the automobile 10. In the automobile 100, a pair of speakers 108*a* and 108*b* are separately installed at the left and right of the back of a rear seat in the vehicle body 101. The speakers 108*a* and 108*b* are disposed in such orientation that the sound produced by each speaker propagates in a direction from the engine 102 toward the cabin.

A rotation sensor 103 is provided on the engine 102. The remaining components of the vehicle sound generation apparatus included in the automobile 100 are the same as those of the above-described automobile 20. In the automobile 100, the speakers 108*a* and 108*b* are separately disposed at the left and right of the back of the rear seat in a vehicle body 101 such that the sound produced by each speaker propagates in a direction from the engine 102 disposed at the back of the vehicle body 101 toward the cabin. By virtue of this, the occupants can feel that the intake sound output from the speakers 108*a* and 108*b* comes from the engine 102. As a result, the occupants can feel this sound to be the actual intake sound of the engine 102.

The number of speakers included in the vehicle sound generation apparatus according to the present invention may be odd or even. When an odd number of speakers are used, preferably, a speaker is disposed at the center of the vehicle in the widthwise direction. This prevents the intake sound from coming from either the left or right side of the vehicle, thereby improving the localization of sound. Speakers may be disposed in hidden spaces, such as inside the dashboard provided at the front of the cabin of the vehicle, or exposed spaces in the cabin. However, preferably, each speaker is secured directly to a vehicle-body-side portion, for example, the wall panel of the dashboard. By doing so, the occupants feel that the intake sound comes from a deeper position in the vehicle body and is changing naturally. In addition, propagation of vibrations through the vehicle body allows the occupants to feel the intake sound coming from every part of the vehicle body.

The above-described speaker 28*a*, 28*b*, etc. may be provided as dedicated speakers of the vehicle sound generation apparatus 20, etc., or may be the speakers of audio equipment provided in the automobile 10, etc. In the above-described first and second embodiments, the signal processing section 24 performs processing of changing the level of the sound pressure signal by use of two parameters; i.e., the engine speed detected by the rotation sensor 31 and the throttle opening detected by the opening sensor 32. However, the signal processing section 24 may perform this processing by using, as an additional parameter, the traveling speed of the automobile detected by the vehicle speed sensor 33.

In the above-described embodiments, the vehicle sound generation apparatus includes a single first pressure sensor and a single second pressure sensor. However, the vehicle sound generation apparatus may include a plurality of first pressure sensors and/or a plurality of second pressure sensors. In this case, the first pressure sensors may be disposed on the circumferential wall of the intake duct such that they are lined in the circumferential direction or in the longitudinal direction of the intake duct. Preferably, the second pressure sensors are disposed on an outer wall surface of the surge tank, etc. such that they are spaced from one another. By doing so, the pressure signal can be amplified, and sounds corresponding to various portions of the engine can be produced.

The invention claimed is:

1. A vehicle sound generation apparatus for transmitting an intake sound of an engine of a vehicle to an occupant in the vehicle, characterized by comprising:

- a first pressure sensor which is provided on an intake duct, the intake duct connects an air cleaner provided on a side of the intake duct toward an intake port that introduces external air and a throttle body provided on a side of the intake duct toward the engine, the first pressure sensor being located on the air cleaner side of a midpoint between the air cleaner and a throttle valve provided in the throttle body, detecting pressure of intake pulsation of the engine, and outputting a pressure signal representing the detected pressure;
- a second pressure sensor which is provided between the engine and the throttle valve and which detects the pressure of the intake pulsation of the engine and outputs a pressure signal representing the detected pressure;
- a signal processor which performs processing of changing the pressure signals output from the first and second pressure sensors in accordance with an operation state of the vehicle;
- a speaker disposed in the vehicle and outputting the pressure signals processed by the signal processor as the intake sound of the engine; and
- a noise gate processor which performs noise gate processing on the pressure signals before being processed by the signal processor.

2. A vehicle sound generation apparatus according to claim 1, further comprising a noise suppression processor which performs noise suppression processing on the pressure signals before or after being processed by the signal processor.

3. A vehicle sound generation apparatus according to claim 1, further comprising a filter prepared on the basis of a relation between frequency and gain, wherein the signal processor performs the processing of changing the pressure signals by using the filter.

4. A vehicle sound generation apparatus according to claim 1, wherein an air flow meter that detects the flow rate of air is provided on the intake duct to be located in the vicinity of and on the downstream side of the air cleaner, and the first pressure sensor is provided at a position which is offset from the air flow meter toward the throttle valve by an amount of 20 cm or less.

5. A vehicle sound generation apparatus according to claim 1, further comprising a communication portion which extends outward from a circumferential wall of the intake duct, wherein a pressure sensing portion of the first pressure sensor is disposed at a distal end of the communication portion, and a passage length of the communication portion between its base end portion on the intake duct side and the pressure sensing portion of the first pressure sensor is set to a length equal to or less than a length which causes resonance of the communication portion.

6. A vehicle sound generation apparatus according to claim 5, further comprising a communication portion which extends outward from a portion which is located between the engine and the throttle valve and to which the second pressure sensor is attached, wherein a pressure sensing portion of the second pressure sensor is disposed at a distal end of the communication portion, and a passage length of the communication portion between its base end portion and the pressure sensing portion of the second pressure sensor is set to a length equal to or greater than the passage length of the communication portion for the first pressure senor between the base end portion and the pressure sensing portion of the first pressure sensor.

7. A vehicle sound generation apparatus according to claim 6, wherein the passage length of the communication portion between the base end portion and the pressure sensing portion of the second pressure sensor is set to a length between 4 cm and 50 cm.

8. A vehicle sound generation apparatus according to claim 1, wherein each of the first pressure sensor and the second pressure sensor measures both of positive and negative pressures.

9. A vehicle sound generation apparatus according to claim 1, wherein the DC component of a signal output from the first pressure sensor is removed by a filter.

10. A vehicle sound generation apparatus according to claim 1, wherein the engine is an independent throttle type in which throttle bodies are independently provided for cylinders, the throttle bodies communicate with one another through a balance pipe portion on the downstream side of the throttle valves provided in the throttle bodies, and the second pressure sensor is provided on the balance pipe portion.

11. A vehicle sound generation apparatus according to claim 1, wherein the engine has a turbo charger including a compressor located at an intermediate portion of the intake duct, and the first pressure sensor is provided at a position between the compressor and the air cleaner.

12. A vehicle sound generation apparatus according to claim 1, wherein the second pressure sensor outputs a pulsating signal including an AC component and a DC component.

13. A vehicle sound generation apparatus for transmitting an intake sound of an engine of a vehicle to an occupant in the vehicle, characterized by comprising:

a first pressure sensor which is provided on an intake duct, the intake duct connects an air cleaner provided on a side of the intake duct toward an intake port that introduces external air and a throttle body provided on a side of the intake duct toward the engine, the first pressure sensor being located on the air cleaner side of a midpoint between the air cleaner and a throttle valve provided in the throttle body, detecting pressure of intake pulsation of the engine, and outputting a pressure signal representing the detected pressure;

a second pressure sensor which is provided between the engine and the throttle valve and which detects the pressure of the intake pulsation of the engine and outputs a pressure signal representing the detected pressure;

a signal processor which performs processing of changing the pressure signals output from the first and second pressure sensors in accordance with an operation state of the vehicle;

a speaker disposed in the vehicle and outputting the pressure signals processed by the signal processor as the intake sound of the engine; and a rotation sensor that detects a rotational speed of the engine, an opening sensor that detects an opening of the throttle valve, and a sound pressure amplification map prepared on the basis of a relation between the rotational speed of the engine detected by the rotation sensor and the throttle opening detected by the opening sensor, wherein the signal processor performs sound pressure amplification processing on the pressure signals by using the sound pressure amplification map.

14. A vehicle sound generation apparatus for transmitting an intake sound of an engine of a vehicle to an occupant in the vehicle, characterized by comprising:

a first pressure sensor which is provided on an intake duct, the intake duct connects an air cleaner provided on a side of the intake duct toward an intake port that introduces external air and a throttle body provided on a side of the intake duct toward the engine, the first pressure sensor being located on the air cleaner side of a midpoint between the air cleaner and a throttle valve provided in the throttle body, detecting pressure of intake pulsation of the engine, and outputting a pressure signal representing the detected pressure;

a second pressure sensor which is provided between the engine and the throttle valve and which detects the pressure of the intake pulsation of the engine and outputs a pressure signal representing the detected pressure;

a signal processor which performs processing of changing the pressure signals output from the first and second pressure sensors in accordance with an operation state of the vehicle;

a speaker disposed in the vehicle and outputting the pressure signals processed by the signal processor as the intake sound of the engine; and A a rotation sensor that detects a rotational speed of the engine and a gain adjustment map which is prepared on the basis of a relation between frequency and gain, wherein the signal processor obtains a frequency from the rotational speed of the engine detected by the rotation sensor and the number of cylinders of the engine, and adjusts a gain for the pressure signals by using the obtained frequency and the gain adjustment map.

15. A vehicle sound generation apparatus for transmitting an intake sound of an engine of a vehicle to an occupant in the vehicle, characterized by comprising:

a first pressure sensor which is provided on an intake duct, the intake duct connects an air cleaner provided on a side of the intake duct toward an intake port that introduces external air and a throttle body provided on a side of the intake duct toward the engine, the first pressure sensor being located on the air cleaner side of a midpoint between the air cleaner and a throttle valve provided in the throttle body, detecting pressure of intake pulsation of the engine, and outputting a pressure signal representing the detected pressure;

a second pressure sensor which is provided between the engine and the throttle valve and which detects the pressure of the intake pulsation of the engine and outputs a pressure signal representing the detected pressure;

a signal processor which performs processing of changing the pressure signals output from the first and second pressure sensors in accordance with an operation state of the vehicle;

a speaker disposed in the vehicle and outputting the pressure signals processed by the signal processor as the intake sound of the engine; and a rotation sensor that detects a rotational speed of the engine, an opening sensor that detects an opening of the throttle valve, and an effector processing map which is prepared on the basis of a relation between the rotational speed of the engine detected by the rotation sensor and the throttle opening detected by the opening sensor and which has a compressor processing region and a reverberator processing region, wherein the signal processor performs compressor processing or reverberator processing on the pressure signals by using the effector processing map.

16. A vehicle sound generation apparatus according to claim 15, wherein the compressor processing is performed when both of the value of the rotational speed of the engine detected by the rotation sensor and the value of the throttle opening detected by the opening sensor are small, and reverberator processing is performed when one or both of the value of the rotational speed of the engine detected by the rotation sensor and the value of the throttle opening detected by the opening sensor are large.

17. A vehicle sound generation apparatus for transmitting an intake sound of an engine of a vehicle to an occupant in the vehicle, characterized by comprising:

a first pressure sensor which is provided on an intake duct, the intake duct connects an air cleaner provided on a side of the intake duct toward an intake port that introduces external air and a throttle body provided on a side of the intake duct toward the engine, the first pressure sensor being located on the air cleaner side of a midpoint between the air cleaner and a throttle valve provided in the throttle body, detecting pressure of intake pulsation of the engine, and outputting a pressure signal representing the detected pressure;

a second pressure sensor which is provided between the engine and the throttle valve and which detects the pressure of the intake pulsation of the engine and outputs a pressure signal representing the detected pressure;

a signal processor which performs processing of changing the pressure signals output from the first and second pressure sensors in accordance with an operation state of the vehicle;

a speaker disposed in the vehicle and outputting the pressure signals processed by the signal processor as the intake sound of the engine; and an acceleration sensor that detects an acceleration of the vehicle, and a sound pressure amplification map which is prepared on the basis of the acceleration of the vehicle detected by the acceleration sensor, wherein the signal processor performs sound pressure amplification processing on the pressure signals by using the sound pressure amplification map.

* * * * *